(12) United States Patent
Kozikowski et al.

(10) Patent No.: US 7,378,403 B2
(45) Date of Patent: May 27, 2008

(54) AKT INHIBITORS, PHARMACEUTICAL COMPOSITIONS, AND USES THEREOF

(75) Inventors: Alan P. Kozikowski, Chicago, IL (US); Phillip Dennis, Ellicott City, MD (US); Haiying Sun, Ann Arbor, MI (US); John Brognard, Carlsbad, CA (US)

(73) Assignees: The United States of America as represented by the Department of Health and Human Services, Washington, DC (US); Georgetown University, Washington, DC (US)

( * ) Notice: Subject to any disclaimer, the term of this patent is extended or adjusted under 35 U.S.C. 154(b) by 84 days.

(21) Appl. No.: 10/526,851

(22) PCT Filed: Sep. 3, 2003

(86) PCT No.: PCT/US03/27607

§ 371 (c)(1),
(2), (4) Date: May 19, 2005

(87) PCT Pub. No.: WO2004/022569

PCT Pub. Date: Mar. 18, 2004

(65) Prior Publication Data

US 2005/0272708 A1  Dec. 8, 2005

Related U.S. Application Data

(60) Provisional application No. 60/407,239, filed on Sep. 3, 2002.

(51) Int. Cl.
*A61K 31/662* (2006.01)
*A61K 31/683* (2006.01)
*C07F 9/09* (2006.01)
*C07F 9/30* (2006.01)

(52) U.S. Cl. ........................ 514/129; 558/186
(58) Field of Classification Search ................ 558/186; 514/129
See application file for complete search history.

(56) References Cited

U.S. PATENT DOCUMENTS 4,585,762 A * 4/1986 Teraji et al. ................ 514/129
4,783,402 A * 11/1988 Kokusho et al. ............ 435/52
5,227,508 A 7/1993 Kozikowski et al.

FOREIGN PATENT DOCUMENTS

WO  WO 00/00206 A1  1/2000

OTHER PUBLICATIONS

Indicates CAS Abstract attached.*
Smith, M. B. Organic Synthesis, McGraw-Hill, Inc. 1994, Chapter 1.*
Kumar et al. Oncogene 2005, 24, 7493-7501.*
Vizitiu et al. J. Molecular Recognition 1996, 9(2), 197-209.*

Ryan et al. J. Med. Chem. 1996, 39(22), 4366-4376.*
Qiao et al., *J. Med. Chem.*, 41(18), 3303-3306 (1998).
Balendran et al., PDK1 acquires PDK2 activity in the presence of a synthetic peptide derived from the carboxyl terminus of PRK2, *Curr Biol.*, 9, 393-404 (1999).
Bellacosa et al., P. N. A retroviral oncogene, akt, encoding a serine-threonine kinase containing an SH2-like region, *Science*, 254, 274-277 (1991).
Blair et al., Akt-dependent potentiation of L channels by insulin-like growth factor- 1 is required for neuronal survival, *J Neurosci*, 19, 1940-1951 (1999).
Brognard et al., Akt/protein kinase b is constitutively active in non-small cell lung cancer cells and promotes cellular survival and resistance to chemotherapy and radiation, *Cancer Res.*, 61, 3986-3997 (2001).

(Continued)

*Primary Examiner*—Kamal A. Saeed
*Assistant Examiner*—Jason M Nolan
(74) *Attorney, Agent, or Firm*—Leydig, Voit & Mayer, Ltd.

(57) ABSTRACT

Disclosed are inhibitors of the serine/threonine kinase Akt, pharmaceutical compositions comprising such inhibitors, and a method of preventing or treating a disease or condition in an animal by the use of such inhibitors. The Akt inhibitors have the formula (I) wherein X and Y are independently selected from the group consisting of O, $CF_2$, $CH_2$, and CHF; wherein A is independently selected from the group consisting of P(O)OH, $CH_2OOOH$, and $CH(COOH)_2$; $R_2$ is selected from the group consisting of H, OH, isosteres of OH, $C_1$-$C_{25}$ alkyloxy, $C_6$-$C_{10}$ aryloxy, $C_3$-$C_8$ cycloalkyloxy, $C_3$-$C_8$ cycloalkyl $C_1$-$C_6$ alkoxy, $C_2$-$C_{22}$ alkenyloxy, $C_3$-$C_8$ cycloalkenyloxy, $C_7$-$C_{32}$ aralkyloxy, $C_7$-$C_{32}$ alkylaryloxy, $C_9$-$C_{32}$ aralkenyloxy, and $C_9$-$C_{32}$ alkenylaryloxy; $R_3$-$R_6$ are independently selected from the group consisting of H, OH, isosteres of OH; and $R_1$ and $R_7$ are independently selected from the group consisting of $C_1$-$C_{25}$ alkyl, $C_6$-$C_{10}$ aryl, $C_3$-$C_8$ cycloalkyl, $C_2$-$C_{22}$ alkenyl, $C_3$-$C_8$ cycloalkenyl, $C_7$-$C_{32}$ aralkyl, $C_7$-$C_{32}$ alkylaryl, $C_9$-$C_{32}$ aralkenyl, and $C_9$-$C_{32}$ alkenylaryl; with the provisos that (i) when X is O, Y is O or $CH_2$, and $R_3$ is H, at least one of $R_2$ and $R_4$-$R_6$ is not OH; (ii) when A is $CH_2COOH$ or $CH(COOH)_2$, X and Y cannot be simultaneously O; and (iii) all of $R_2$-$R_6$ are not simultaneously H. The inhibitors can be in the form of a salt also

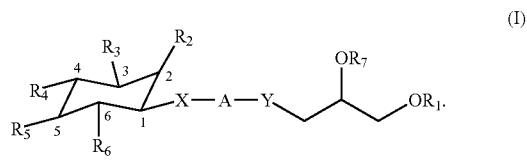

54 Claims, 13 Drawing Sheets

OTHER PUBLICATIONS

Brunet et al., Akt promotes cell survival by phosphorylating and inhibiting a Forkhead transcription factor, *Cell*, 96, 857-868 (1999).

Cardone et al., Regulation of cell death protease caspase-9 by phosphorylation, *Science*, 282, 1318-1321 (1998).

Chalecka-Franaszek et al., Lithium activates the serine/threonine kinase Akt-1 and suppresses glutamate-induced inhibition of Akt-1 activity in neurons, *Proc Natl Acad Sci U S A*, 96, 8745-8750 (1999).

Chen et al., Suppression of transforming growth factor-β-induced apoptosis through a phosphatidylinositol 3-kinase/Akt-dependent pathway, *Oncogene*, 17, 1959-1968 (1998).

Clark et al., Constitutive and inducible Akt activity promotes resistance to chemotherapy, trastuzumab, and tamoxifen in breast cancer cells, *Molec Canc Ther.*, 1, 707-717 (2002).

Coffer et al., Molecular cloning and characterisation of a novel putative protein-serine kinase related to the cAMP-dependent and protein kinase C families, *Eur J Biochem.*, 201, 475-481 (1991).

Crowder et al., Phosphatidylinositol 3-kinase and Akt protein kinase are necessary and sufficient for the survival of nerve growth factor-dependent sympathetic neurons. *J Neurosci*, 18, 2933-2943 (1998).

Datta et al., Akt Phosphorylation of BAD Couples Survival Signals to the Cell-Intrinsic Death Machinery, *Cell*, 91, 231-241 (1997).

Datta et al., Cellular survival: a play in three Akts, *Genes Dev.*, 13, 2905-2927 (1999).

Del Peso et al., Interleukin-3-induced phosphorylation of BAD through the protein kinase Akt., *Science*, 278, 687-689 (1997).

Delcommenne et al., Phosphoinositide-3-OH kinase-dependent regulation of glycogen synthase kinase 3 and protein kinase B/AKT by the integrin-linked kinase, *Proc Natl Acad Sci U S A*, 95, 11211-11216 (1998).

Dudek et al., Regulation of Neuronal Survival by the Serine-Threonine Protein Kinase Akt, *Science*, 275, 661-665 (1997).

Eves et al., N. Akt, a target of phosphatidylinositol 3-kinase, inhibits apoptosis in a differentiating neuronal cell line, *Mol Cell Biol.*, 18, 2143-2152 (1998).

Filippa et al., Mechanism of protein kinase B activation by cyclic AMP-dependent protein kinase, *Mol Cell Biol.*, 19, 4989-5000 (1999).

Gerber et al., Vascular endothelial growth factor regulates endothelial cell survival through the phosphatidylinositol 3'-kinase/Akt signal transduction pathway, *J Biol Chem.*, 273, 30336-30343 (1998).

Hausler et al., Protection of CD95-mediated apoptosis by activation of phosphatidylinositide 3-kinase and protein kinase B, *Eur J Immunol*, 28, 57-69 (1998).

Hu et al., Synthesis and AKT inhibitory properties of a 1D-3, 4-dideoxyphosphatidylinositol ether lipid, *Tetrahedron Letters*, 41, 7415-7418 (2000).

Jones et al., Molecular cloning and identification of a serine/threonine protein kinase of the second-messenger subfamily, *Proc Natl Acad Sci U S A*, 88, 4171-4175 (1991).

Kang et al., Akt protein kinase enhances human telomerase activity through phosphorylation of telomerase reverse transcriptase subunit, *J Biol Chem.*, 274, 13085-13090 (1999).

Kauffmann-Zeh et al., Suppresion of c-Myc-induced apoptosis by Ras signalling through PI(3)K and PKB, *Nature*, 385, 544-548 (1997).

Kennedy et al., Akt/Protein kinase B inhibits cell death by preventing the release of cytochrome c from mitochondria, *Mol Cell Biol.*, 19, 5800-5810 (1999).

Khwaja et al., Matrix adhesion and Ras transformation both activate a phosphoinositide 3-OH kinase and protein kinase B/Akt cellular survival pathway, *The EMBO Journal*, 16, 2783-2793 (1997).

Kops et al., Direct control of the Forkhead transcription factor AFX by protein kinase B, *Nature*, 398, 630-634 (1999).

Kozikowski et al., Synthesis of 1D-3-Deoxy-and-2, 3-Dideoxyphosphatidylinositol., *Tetrahedron*, 53, 14903-14914 (1997).

Kulik et al., Antiapoptotic Signalling by the Insulin-Like Growth Factor I Receptor, Phosphatidylinositol 3-Kinase, and Akt, *Molecular and Cellular Biology*, 17, 1595-1606 (1997).

Kulik et al., Akt-dependent and -independent survival signaling pathways utilized by insulin-like growth factor I, *Molecular and Cellular Biology*, 18, 6711-6718 (1998).

Lynch et al., Integrin-linked kinase regulates phosphorylation of serine 473 of protein kinase B by an indirect mechanism, *Oncogene*, 18: 8024-8032 (1999).

Ozes et al., NF-κB activation by tumour necrosis factor requires the Akt serine- threonine kinase, *Nature*, 401, 82-85 (1999).

Qiao et al., A Versatile Approach to PI(3,4) $P_2$, PI(4,5)$P_2$, and PI(3,4,5)$P_3$ from L-(-)-Quebrachitol, *Organic Letters*, 2, 115-117 (2000); Published on Web Dec. 22, 1999.

Rohn et al., The opposing roles of the Akt and c-Myc signalling pathways in survival from CD95-mediated apoptosis, *Oncogene*, 17, 2811-2818 (1998).

Romashkova et al., NF-κB is a target of AKT in anti-apoptotic PDGF signaling, *Nature*, 401, 86-90 (1999).

Rust et al., The bile acid taurochenodeoxycholate activates a phosphatidylinositol 3-kinase-dependent survival signaling cascade, *J Biol Chem.*, 275, 20210-20216 (2000).

Testa et al., AKT plays a central role in tumorigenesis, *Proc Natl Acad Sci U S A*, 98, 10983-10985 (2001).

Toker et al., Akt/protein kinase B is regulated by autophosphorylation at the hypothetical PDK-2 site, *J Biol Chem.*, 275, 8271-8274 (2000).

Yano et al., Calcium promotes cell survival through CaM-K kinase activation of the protein-kinase-B pathway, *Nature*, 396, 584-587 (1998).

\* cited by examiner

SH-19

MW 577.74
Weight 3.93 mg
Solubility DMSO

SH-20

MW 830.78
Weight 5.06 mg
Solubility DMSO

SH-21

MW 858.82
Weight 5.54 mg
Solubility DMSO

SH-22

MW 798.78
Weight 5.90 mg
Solubility DMSO

SH-23

$C_{32}H_{65}O_{10}P$
MW 640.83
Weight 4.01 mg
Solubility DMSO

SH-24

$C_{36}H_{69}O_{10}P$
MW 680.89
Weight 4.85 mg
Solubility DMSO

SH-25

$C_{28}H_{57}O_9P$
MW 568.72
Weight 4.05 mg
Solubility DMSO

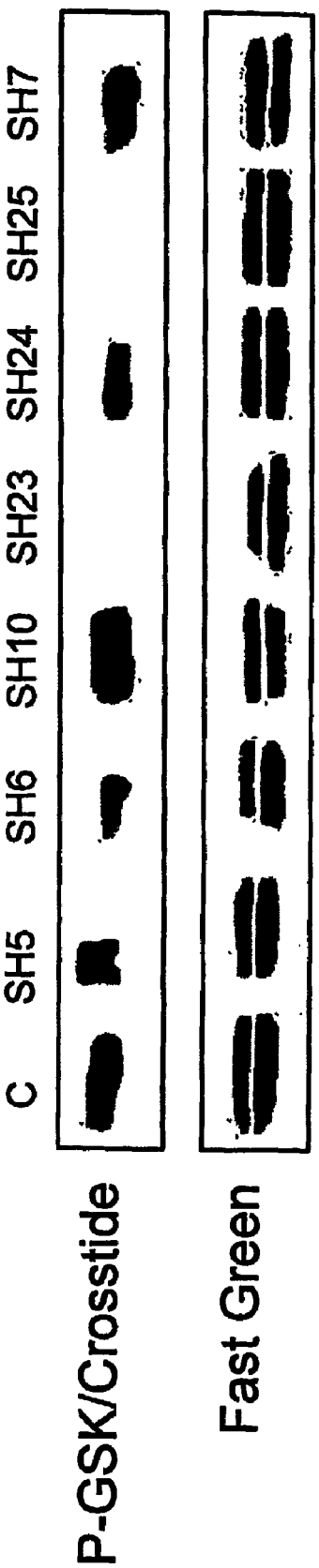

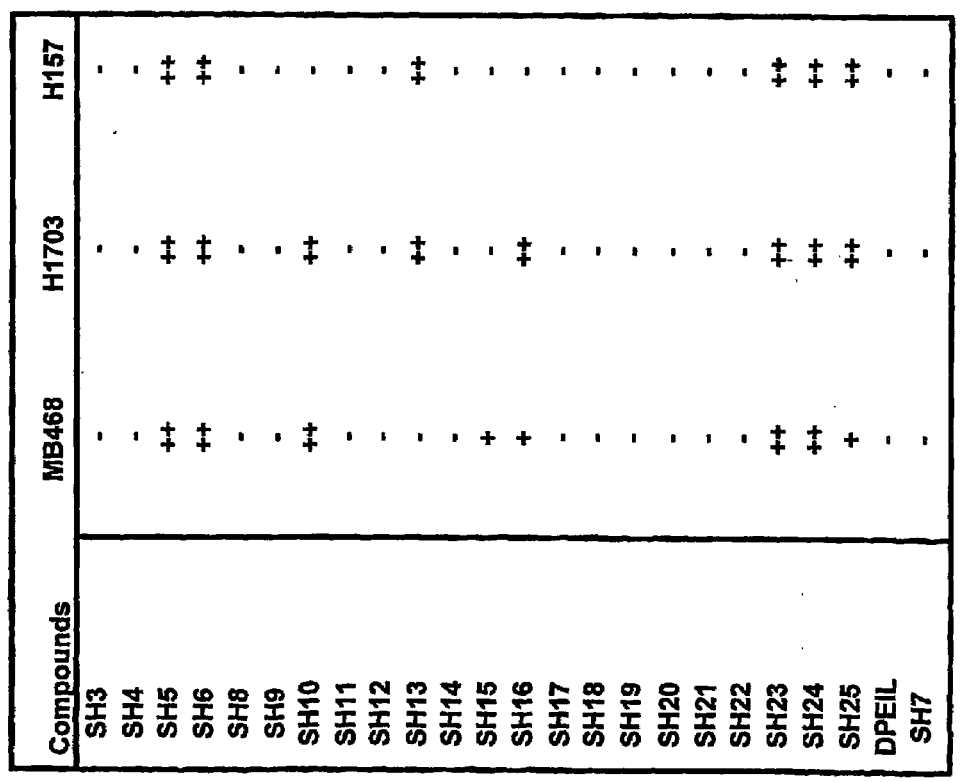

AKT INHIBITORS, PHARMACEUTICAL COMPOSITIONS, AND USES THEREOF

CROSS-REFERENCE TO RELATED APPLICATION

This application claims the benefit of U.S. Provisional Application No. 60/407,239, filed Sep. 3, 2002, the disclosure of which is incorporated by reference.

FIELD OF THE INVENTION

This invention pertains to inhibitors of the serine/threonine kinase Akt, pharmaceutical compositions, and a method of preventing or treating of diseases activated by Akt.

BACKGROUND OF THE INVENTION

Akt (or protein kinase B (PKB)) is a well-characterized serine/threonine kinase that promotes cellular survival. Akt is activated in response to many different growth factors, including IGF-I, EGF, bFGF, insulin, interleukin-3, interleukin-6, heregulin, and VEGF (1). Akt is the cellular homologue of the product of the v-akt oncogene (2-4) and has 3 isoforms, Akt 1, 2, and 3 (or PKB α, β, and γ). Activation of all three isoforms is similar in that phosphorylation of two sites, one in the activation domain and one in the C-terminal hydrophobic motif, are necessary for full activity.

For Akt 1, phosphorylation of T308 in the activation domain by PDK1 is dependent on the products of phosphatidylinositol (PI) 3-kinase (PI3-K), phosphatidylinositol 3,4 bisphosphate ($PIP_2$) and phosphatidylinositol 3,4,5 trisphosphate ($PIP_3$). Cellular levels of $PIP_2$ and $PIP_3$ are controlled by the tumor suppressor, dual-phosphatase PTEN, which dephosphorylates $PIP_2$ and $PIP_3$ at the 3'-position. The mechanism of S473 phosphorylation is less clear. Kinases potentially responsible for S473 phosphorylation include PDK1 (5), ILK or an ILK-associated kinase (6, 7), Akt itself (8) or an as yet uncharacterized PDK2. Akt activation may also be achieved through PI3-K independent means, by phosphorylation of Akt by kinases such as PKA (9) or CAM-KK (10). Once activated, Akt exerts anti-apoptotic effects through phosphorylation of substrates that directly regulate the apoptotic machinery such as Bad (11, 12) or caspase 9 (13), or phosphorylation of substrates that indirectly inhibit apoptosis such the human telomerase reverse transcriptase subunit (hTERT) (14), forkhead transcription family members (15, 16), or IκB kinases (17, 18).

Functionally, Akt promotes survival in vitro when cells are exposed to different apoptotic stimuli such as GF withdrawal, UV irradiation, matrix detachment, cell cycle discordance, DNA damage, and administration of anti-Fas antibody, TGF-β, glutamate, or bile acids (19-33). In vivo, activation of the PI3K/Akt pathway contributes to tumorigenesis in many types of tissues, including breast, ovarian, brain, prostate, and lymph tissues (34). It has been shown that Akt is constitutively active in over 90% of NSCLC cell lines and contributes to both chemotherapeutic resistance and radiation resistance (35). In addition, it has been shown that Akt is constitutively active in many breast cancer cell lines, and serves a similar function in promotion of cellular survival and chemotherapeutic resistance (36).

The foregoing shows that inhibitors of Akt would be desirable for preventing or treating a number of diseases, especially diseases such as cancer.

The advantages of the invention, as well as additional inventive features, will be apparent from the description of the invention provided herein.

BRIEF SUMMARY OF THE INVENTION

The invention provides compounds which are inhibitors of the Akt, pharmaceutical compositions comprising such an inhibitor and a pharmaceutically acceptable carrier, and a method of preventing or treating diseases by the use of such inhibitors. The inhibitors include phosphoinositol ether lipid analogues as well as bioisosteres thereof.

BRIEF DESCRIPTION OF THE DRAWINGS

FIG. 1E depicts the effect of some of the Akt inhibitors on Akt kinase activity.

FIG. 1F depicts inhibition of Akt phosphorylation by some of the compounds of the invention.

DETAILED DESCRIPTION OF THE INVENTION

Figure 1A:
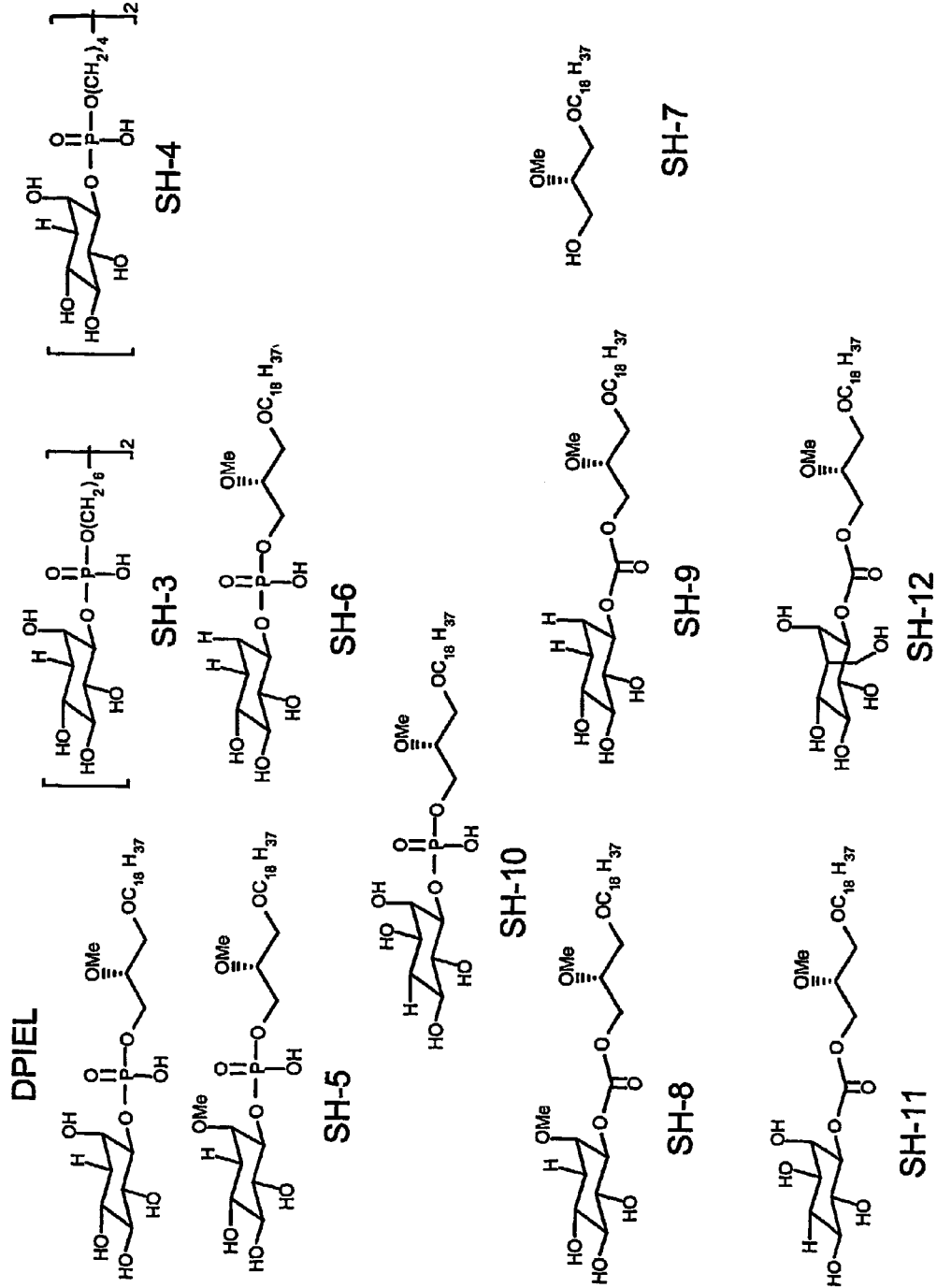
FIG. 1A depicts the formulas of some of the Akt inhibitors.

The present invention provides a compound of the formula I:

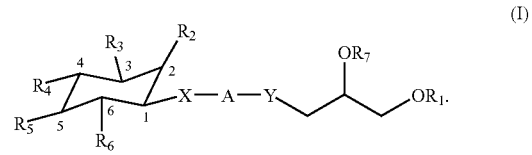

or a pharmaceutically acceptable salt thereof;

wherein X and Y are independently selected from the group consisting of O, $CF_2$, $CH_2$, and CHF;

A is independently selected from the group consisting of P(O)OH, CHCOOH, and $C(COOH)_2$;

$R_2$ is selected from the group consisting of H, OH, isosteres of OH, $C_1$-$C_{25}$ alkyloxy, C6-$C_{10}$ aryloxy, $C_3$-$C_8$ cycloalkyloxy, $C_3$-$C_8$ cycloalkyl C1-C6 alkoxy, $C_2$-$C_{22}$ alkenyloxy, $C_3$-$C_8$ cycloalkenyloxy, $C_7$-$C_{32}$ aralkyloxy, $C_7$-$C_{32}$ alkylaryloxy, C9-C32 aralkenyloxy, and $C_9$-$C_{32}$ alkenylaryloxy;

$R_3$-$R_6$ are independently selected from the group consisting of H, OH, isosteres of OH; and $R_1$ and $R_7$ are independently selected from the group consisting of $C_1$-$C_{25}$ alkyl, $C_6$-$C_{10}$ aryl, $C_3$-$C_8$ cycloalkyl, $C_2$-$C_{22}$ alkenyl, $C_3$-$C_8$ cycloalkenyl, $C_7$-$C_{32}$ aralkyl, $C_7$-$C_{32}$ alkylaryl, $C_8$-$C_{32}$ aralkenyl, and $C_8$-$C_{32}$ alkenylaryl;

with the provisos that (i) when X is O, Y is O or $CH_2$, and $R_3$ is H, at least one of $R_2$ and $R_4$-$R_6$ is not OH; (ii) when A is CHCOOH or $C(COOH)_2$, X and Y cannot be simultaneously O; and (iii) all of $R_2$-$R_6$ are not simultaneously H.

The alkyl and alkenyl portions of $R_1$-$R_7$ can be branched, or preferably linear. The aryl portion of $R_1$-$R_7$ can have one or more aromatic rings of 6-14 carbon atoms, for example, phenyl, naphthyl, or anthracyl rings. Isosteres of OH include F, Cl, SH, and the like.

In a preferred embodiment, A is P(O)OH. In a further preferred embodiment, where A is P(O)OH, both X and Y are O.

The stereochemistry of attachment to the respective carbon atoms of $R_2$ and $OR_7$ can be in any suitable form, e.g., each can be R, S, or a mixture of R and S forms. Thus, for example, the compound of the present invention can have the formula Ia:

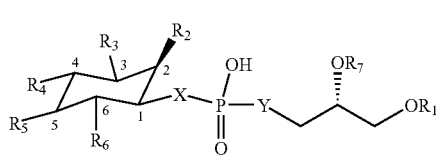

(Ia)

or the formula Ib:

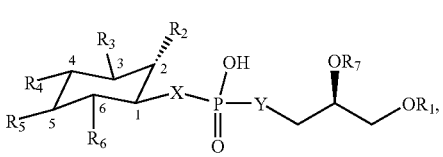

(Ib)

the formula Ia being more preferred.

In some embodiments, compounds of the present invention, particularly those of the formula Ia and Ib, have as $R_1$ a $C_1$-$C_{25}$ alkyl, preferably a $C_{10}$-$C_{25}$ alkyl, and more preferably a $C_{15}$-$C_{20}$ alkyl. Thus, for example, a particular $R_1$ is a $C_1$-8 alky, e.g., n-$C_{18}H_{37}$. In certain embodiments, the compounds of the present invention have as $R_7$ a $C_1$-$C_{25}$ alkyl, preferably a $C_1$-$C_{15}$ alkyl, more preferably a $C_1$-$C_5$ alkyl. Thus, for example, a particular $R_7$ is methyl. In particularly preferred embodiments, $R_1$ is a CIS alkyl (e.g., n-$C_{18}H_{37}$) and $R_7$ is methyl.

In certain embodiments, compounds of the present invention, particularly those of the formula Ia and Ib, have as $R_2$ a $C_1$-$C_{25}$ alkyloxy, preferably a $C_1$-$C_{15}$ alkyloxy, more preferably a $C_1$-$C_5$ alkyloxy. A particular $R_2$ is methoxy. In certain other embodiments, $R_2$ is $C_7$-$C_{32}$ aralkyloxy, and in some other embodiments, $R_2$ is $C_3$-$C_8$ cycloalkyloxy, or $C_3$-$C_8$ cycloalkyl $C_1$-$C_6$ alkoxy, e.g., cyclohexylmethyloxy.

In embodiments of the present invention, at least one of $R_2$, $R_3$, $R_4$, $R_5$, or $R_6$ is H, for example, $R_2$ and $R_3$ are H, $R_3$ and R are H, or $R_5$ and $R_6$ are H.

Figure 1B:
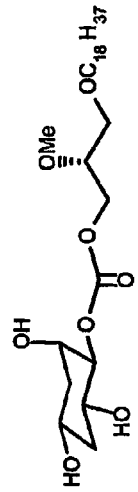
FIG. 1B depicts the formulas of some other Akt inhibitors.
Figure 1B:
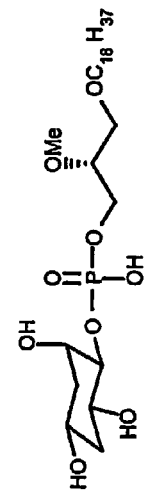
Figure 1B:
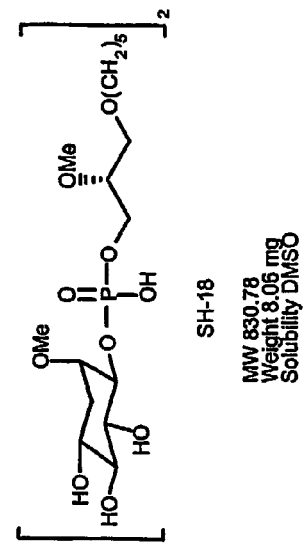
Figure 1B:
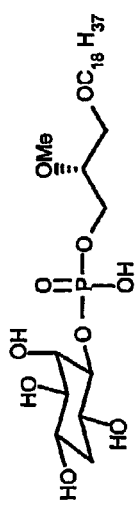
Figure 1B:
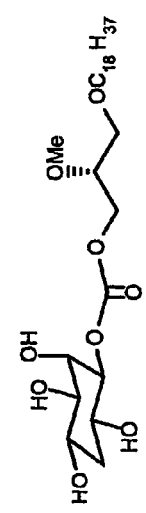
Figure 1B:
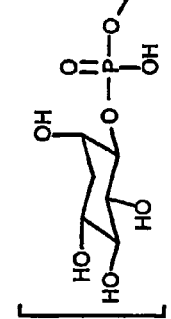
Figure 1C:
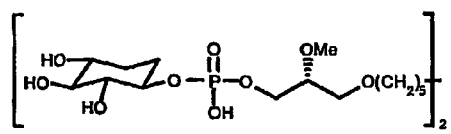
FIG. 1C depicts the formulas of yet other Akt inhibitors.
Figure 1C:
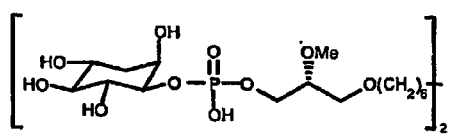
Figure 1C:
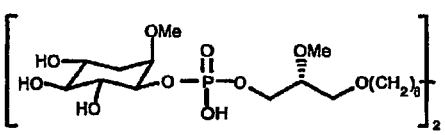
Figure 1C:
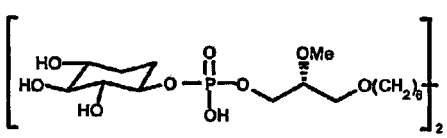
Figure 1C:
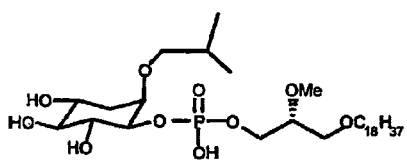
Figure 1C:
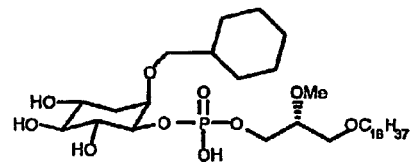
Figure 1C:
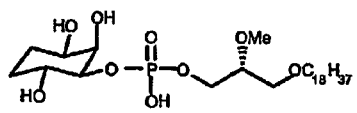

In a preferred embodiment, A is P(O)OH, both X and Y are O, $R_1$ is $C_{18}H_{37}$, and $R_7$ is methyl. For example, in embodiments of the present invention, A is P(O)OH, both X and Y are O, $R_1$ is $C_{18}H_{37}$, and $R_7$ is methyl, and (i) $R_2$ is methoxy, $R_3$ is H, and $R_4$-$R_6$ are OH; (ii) $R_2$-$R_3$ are H and $R_4$-$R_6$ are OH; (iii) $R_2$-$R_3$ and $R_5$-$R_6$ are OH and $R_4$ is H; (iv) $R_2$ is i-butyl, $R_3$ is H, and $R_4$-$R_6$ are OH; (v) $R_2$ is cyclohexylmethoxy, $R_3$ is H, and $R_4$-$R_6$ are OH; (vi) $R_2$-$R_3$ and $R_6$ are OH and $R_4$-$R_5$ are H; (vii) $R_2$-$R_4$ and $R_6$ are OH and $R_5$ is H; or (viii) $R_2$, $R_4$, and $R_6$ are OH and $R_3$ and $R_5$ are H. Some of the compounds of the present invention are shown in FIGS. 1A-1C.

The compounds of the present invention may be in the form of a pharmaceutically acceptable salt, for example, a salt of an alkali metal (e.g., sodium or potassium), alkaline earth metal (e.g., calcium), or ammonium of salt.

The present invention further provides a pharmaceutical composition comprising a compound described above and a pharmaceutically acceptable carrier. The pharmaceutically acceptable (e.g., pharmacologically acceptable) carriers include, for example, vehicles, adjuvants, excipients, or diluents, and are well-known to those who are skilled in the art and are readily available to the public. It is preferred that the pharmaceutically acceptable carrier be one which is chemically inert to the active compounds and one which has little or no detrimental side effects or toxicity under the conditions of use.

The choice of carrier will be determined in part by the particular active compound, as well as by the particular method used to administer the composition. Accordingly, there is a wide variety of suitable formulations of the pharmaceutical composition of the present invention. The composition may be administered in any suitable formulation, for example, as a formulation for oral, aerosol, parenteral, subcutaneous, intravenous, intraarterial, intramuscular, interperitoneal, intrathecal, rectal, or vaginal administration.

Formulations suitable for oral administration can comprise (a) liquid solutions, such as an effective amount of the compound dissolved in diluents, such as water, saline, or orange juice; (b) capsules, sachets, tablets, lozenges, and troches, each containing a predetermined amount of the active ingredient (compound), as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer. Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkylimidazoline quaternary ammonium salts, and (e) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants. The quantity of surfactant in such formulations typically ranges from about 5 to about 15% by weight. Suitable surfactants include polyethylene or polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection-solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The present invention further provides a method of preventing or treating a disease, or a condition that predisposes to a disease, that is characterized by or caused by the activation of the serine/threonine kinase Akt in an animal comprising administering to the animal a preventive or treatment effective amount of a compound described above. An example of a disease or condition is cancer. Particular examples of cancer include breast cancer, lung cancer, ovarian cancer, uterine cancer, brain cancer, sarcoma, melanoma, leukemia, lymphoma, colorectal cancer, prostate cancer, and liver cancer. Another disease or condition is rheumatologic disease, e.g., rheumatoid arthritis or osteoarthritis. A further example of the disease or condition is pulmonary disease, e.g., chronic obstructive pulmonary disease (COPD). The present invention further provides a method of increasing apoptosis of a cell, e.g., cancer cell, comprising contacting or treating the cell with a compound described above. The compounds of the present invention can be used as scientific tools to determine the presence of a disease or condition that are characterized by Akt activation.

They could be used alone or combined with other types of therapies to treat disease. Diseases characterized by Akt activation that could benefit from administration of the compounds include all forms of cancer, precancerous lesions, cardiovascular disease, rheumatologic disease, pulmonary disease, dermatologic disease, gynecological diseases, vascular disease, neurologic disease, and infectious disease, including bacterial, viral, retroviral, and parasitic diseases. Moreover, these compounds could be utilized to prevent above said diseases. Assays incorporating these compounds could provide predictive or prognostic value to patients with above said diseases or conditions.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. In proper doses and with suitable administration of certain compounds, the present invention provides for a wide range of responses. Typically the dosages range from about 0.001 to about 1000 mg/kg body weight of the animal being treated/day. Preferred dosages range from about 0.01 to about 10 mg/kg body weight/day, and further preferred dosages range from about 0.01 to about 1 mg/kg body weight/day.

The present invention further provides a method for inhibiting PH domain binding comprising exposing a material containing an PH domain to a compound described above. The present invention further provides a method for determining the presence of a PH domain in a material comprising:

(a) exposing a sample of the material to a PH domain binding compound and obtaining a first binding result;

(b) exposing another sample of the material to a compound of the present invention and obtaining a second binding result; and (c) comparing the first and second binding results to determine whether a PH domain is present in the material.

The following examples further illustrate the invention but, of course, should not be construed as in any way limiting its scope.

EXAMPLE 1

This Example illustrates a method of preparing precursors for 2-modified analogues.

This illustrates a method of preparing precursor for 3-deoxy 2-modified analogues. Compound 1 was prepared from L-(−)-quebrachitol according to a published method (*Tetrahedron*, 53, 14903-14914 (1997)). Selective p-methoxybenzylation of the 1-OH in 1 via a 1,2-O-stannylene intermediate gave compound 2 (Scheme 1).

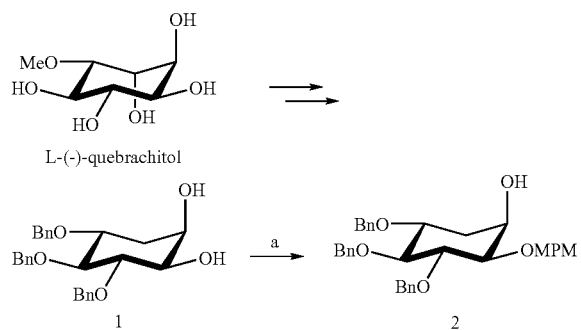

Scheme 1

Reagents and conditions: $Bu_2SnO$, toluene, reflux, then p-$MeOC_6H_4CH_2Cl$, CsF, DMF, rt, 92%.

This illustrates a method of preparing precursors for 4-deoxy 2-modified analogues. Compound 3 was prepared from L-quebrachitol (*Org. Lett.* 2, 115-117 (2000)). After benzyl protection of the 3-OH group, the trans-acetonide was selectively removed to give diol 4. The two hydroxyl groups of 3 were protected by benzylation, and the MPM group at position 4 was removed by oxidation with ceric ammonium nitrate (CAN) to yield alcohol 5. Barton-McCombie deoxygenation at C-4 gave compound 6. Cleavage of the remaining acetonide in 6 gave diol 7. Selective p-methoxybenzylation of the 1-OH of 7 in the same method as 2 gave compound 8 (Scheme 2).

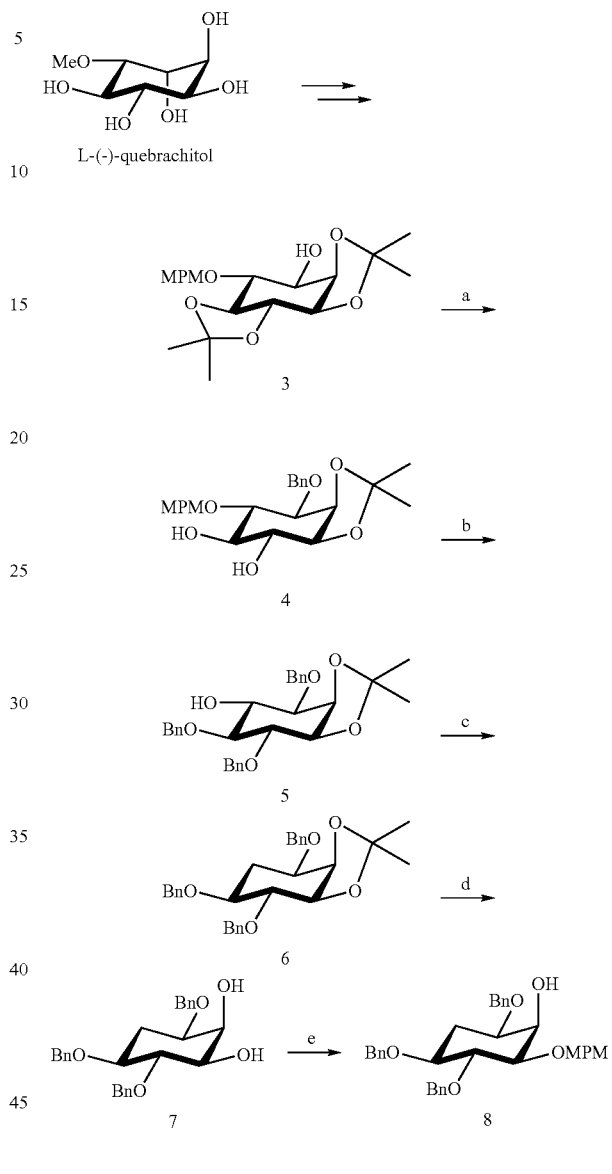

Reagents and conditions: (a) (i) NaH, BnBr, DMF, 0° C.—rt; (ii) AcCl, $CH_2Cl_2$-MeOH 4:1 (v/v), rt, 86% for two steps; (b) (i) NaH, BnBr, 0° C.—rt, DMF; (ii) CAN, $CH_3CN$—$H_2O$ 4:1 (v/v), 0° C.—rt, 84% for two steps; (c) (i) NaH, $CS_2$, 0° C., DMF, then MeI; (ii) $Bu_3SnH$, AIBN, toluene, reflux, 95% for two steps; (d) AcCl, MeOH, rt, 98%; (e) $Bu_2SnO$, toluene, reflux, then p-$MeOC_6H_4CH_2Cl$, CsF, DMF, rt, 93%.

This illustrates a method of preparing a precursor for 5-deoxy-2-modified analogues. Compound 9 was synthesized according to a literature method (*Org. Lett.*, 2, 115-117 (2000)). Mono-benzylation of the diol moiety of 9 via a 4,5-O-stannylene intermediate gave two compounds 5 and 10 in a ratio of 1:1.5, which were separated by careful chromatography on silica gel. Barton-McCombie deoxygenation at C-5 of compound 10 gave compound 11. Cleavage of the trans-acetonide yielded diol 12. Selective p-methoxybenzylation of the 1-OH of 12 in the same method as 2 gave compound 13 (Scheme 3).

Scheme 3

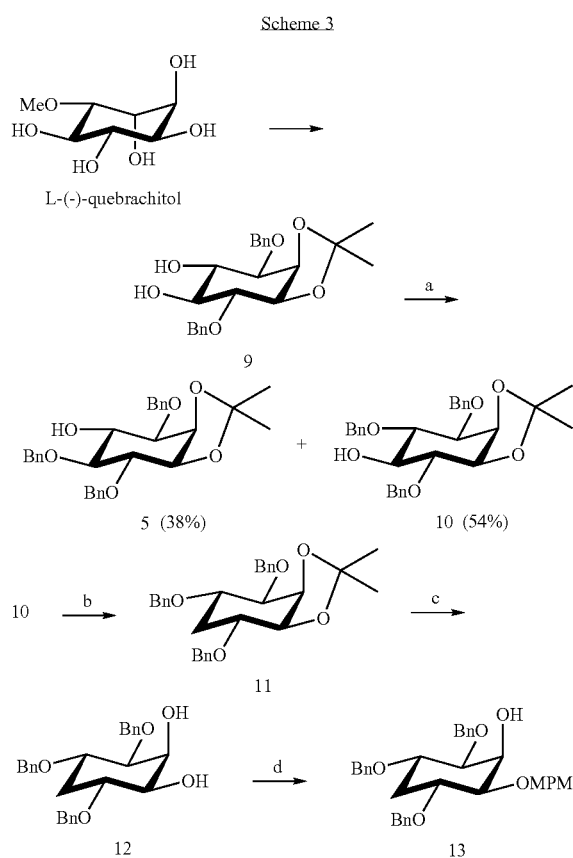

Reagents and conditions: (a) Bu₂SnO, toluene, reflux, then BnBr, CsF, DMF, rt; (b) (i) NaH, CS₂, 0° C., DMF, then MeI; (ii) Bu₃SnH, AIBN, toluene, reflux, 92% for two steps; (c) AcCl, MeOH, rt, 98%; (d) Bu₂SnO, toluene, reflux, then p-MeOC₆H₄CH₂Cl, CsF, DMF, rt, 92%.

This illustrates a method for preparing precursors for 4,5-dideoxy-2-modified analogues. Removal of the two hydroxyl groups in 9 by Barton-McCombie deoxygenation, followed by removal of the trans-acetonide gave olefinic diol 14. Selective hydrogenation of the C=C double bond catalyzed by 5% Pd—C in ethyl acetate gave diol 15. Selective p-methoxybenzylation of the 1-OH of 15 in the same method as 2 give compound 16 (Scheme 4).

Scheme 3

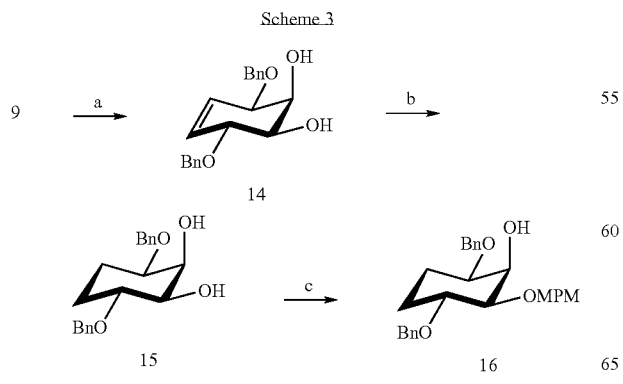

Reagents and conditions: (a) (i) NaH, CS₂, 0° C., DMF, then MeI; (ii) Bu₃SnH, AIBN, toluene, reflux; (iii) AcCl, MeOH, rt, 64% for three steps; (b) H₂, 5% Pd—C, ethyl acetate, rt, 1 atm, 95%; (c) Bu₂SnO, toluene, reflux, then p-MeOC₆H₄CH₂Cl, CsF, DMF, rt, 92%.

This illustrates a method for preparing precursors for 3,5-dideoxoy-2-modified analogues. Compound 17 was synthesized according to a published procedure (*Org. Lett.* 2, 115-117 (2000)). Barton-McCombie deoxygenation at C-3 furnished compound 18. Selective cleavage of the trans-acetonide gave diol 19. Mono-benzylation of the diol moiety gave two compounds 20 and 21 in a ratio of 5:1. The structure of compound 21 was confirmed by transformation into a known intermediate in the synthesis of a 3,4-dideoxy PI analogue (*Tetrahedron Lett.*, 41, 7415-7418 (2000)). Barton-McCombie deoxygenation at C-5 in intermediate 20 gave compound 22. Cleavage of the second acetonide yielded diol 23. Selective p-methoxybenzylation of the 1-OH of 23 in the same method as 2 give compound 24 (Scheme 5).

Scheme 5

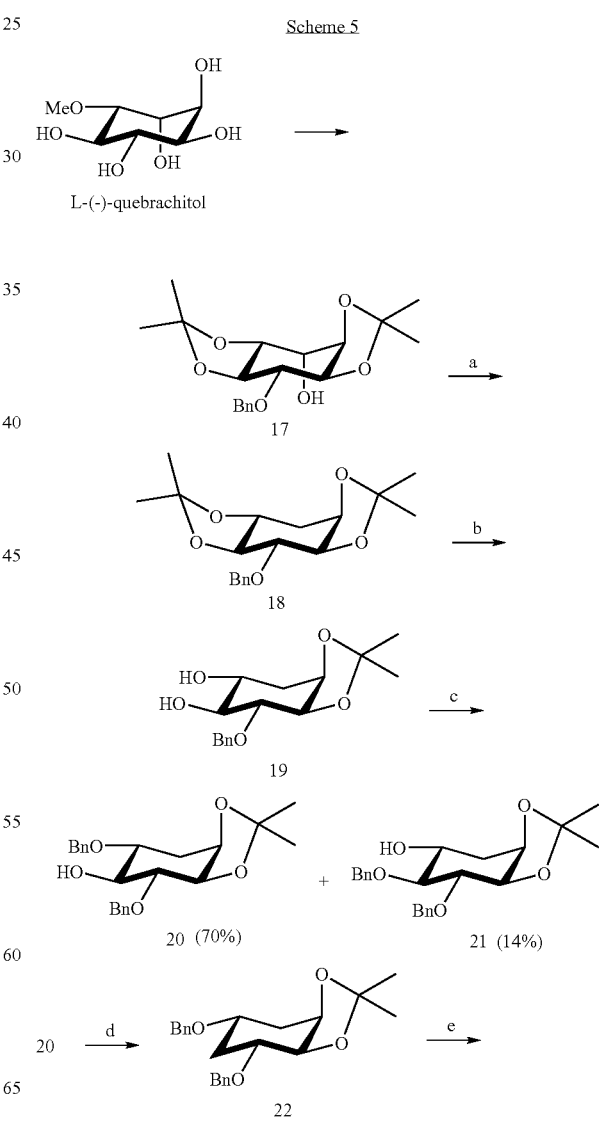

-continued

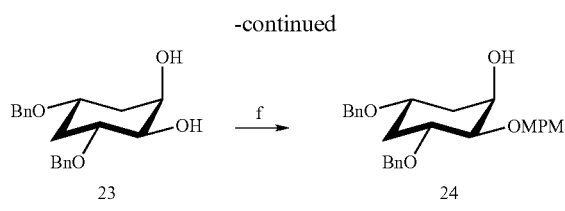

Reagents and conditions: (a) (i) NaH, CS$_2$, 0° C., DMF, then MeI; (ii) Bu$_3$SnH, AIBN, toluene, reflux, 94% for two steps; (b) AcCl, CH$_2$Cl$_2$-MeOH 4:1 (v/v), rt, 86%; (c) Bu$_2$SnO, toluene, reflux, then BnBr, CsF, DMF, rt; (d) (i) NaH, CS$_2$, 0° C., DMF, then MeI; (ii) Bu$_3$SnH, AIBN, toluene, reflux, 93% for two steps; (e) AcCl, MeOH, rt, 96%; (f) Bu$_2$SnO, toluene, reflux, then p-MeOC$_6$H$_4$CH$_2$Cl, CsF, DMF, rt, 93%.

Barton-McCombie deoxygenation at C-2 in compound 2 followed by removal of the MPM group on 1-OH gave compound 25 (Scheme 6).

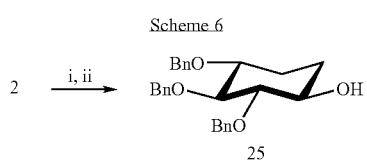

Reagents and conditions: (i) NaH, CS$_2$, then MeI, 0° C., DMF; (ii) Bu$_3$SnH, AIBN, toluene, reflux; (iii) CAN, CH$_3$CN—H$_2$O 4:1 (v/v), 0° C.—rt, 81% over two steps.

This illustrates a method of modifying position 2. The above precursors were alkylated with suitable alkyl halide to give a series of 2-modified compounds. The MPM group in these compounds was cleaved by oxidation with CAN to give a series of precursors for phosphorylation (Scheme 7).

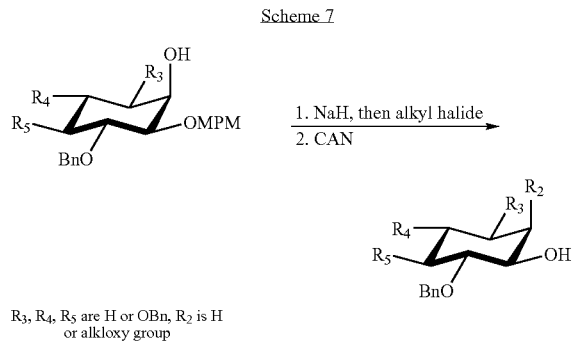

The above precursors were phosphorylated by reaction with the ether lipid phosphoramidite 26 catalyzed by 1H-tetrazole and subsequent oxidation of the phosphite intermediates with m-CPBA to give a series of phosphates. Finally, these phosphates were completely deprotected by catalytic hydrogenation to give the desired analogues (Scheme 8).

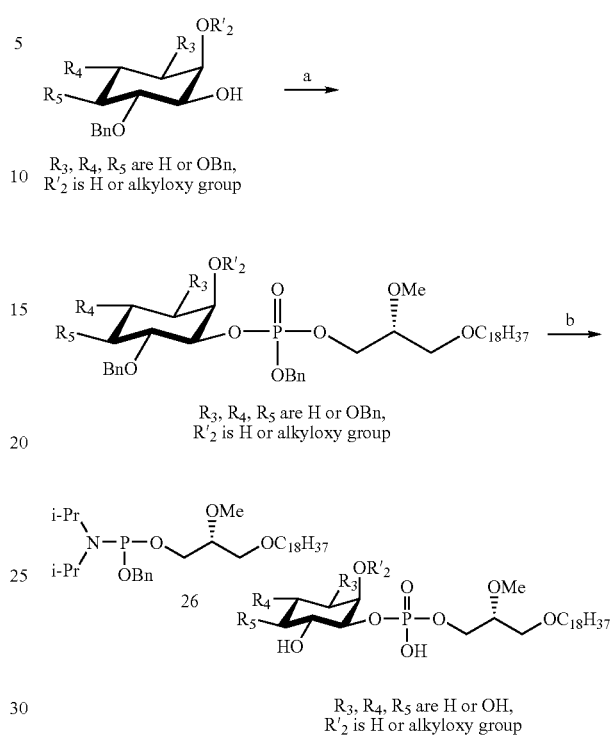

Reagents and conditions: (a) (i) 26, 1H-tetrazole, rt, CH$_2$Cl$_2$; (ii) m-CPBA, 0° C.—rt, CH$_2$Cl$_2$; (b) H$_2$, 20% Pd(OH)$_2$—C, t-BuOH, rt, 1 atm.

EXAMPLE 2

Figure 1D:
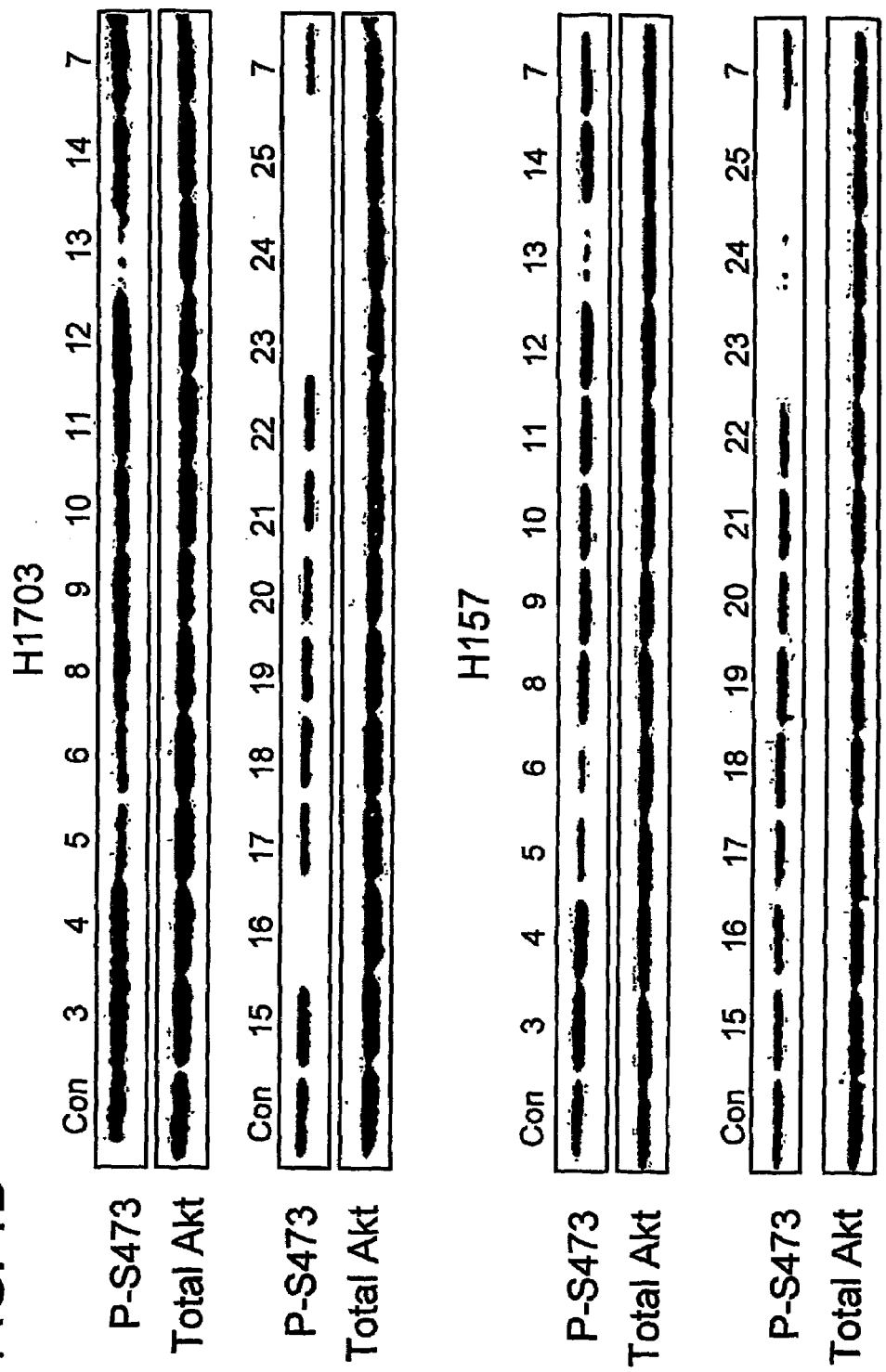
FIG. 1D depicts some of the immunoblots of the Akt inhibitors on S473 phosphorylation ad total Akt levels.

This Example illustrates some of the properties of the compounds of the present invention. FIG. 1D shows results of an immunoblotting experiment performed with antibodies against phosphorylated Akt at S473 and at native Akt after individual administration of the compounds to cancer cell lines. Phospho-specific antibodies only recognize kinases in an active state. Two cell lines were used that have high levels of constitutively active Akt, H1703 and H157. H1703 has wild type PTEN and H157 has mutant PTEN. Compounds SH5, 6, 13, 16, 23, 24, 25 decreased Akt phosphorylation without affecting native Akt levels.

All but SH16 also decreased Akt phosphorylation in the H157-cells. The lack of decreased phosphorylation observed with SH7 is important because SH7 is composed of only the ether lipid portion of these analogues and thus serves as a negative control. This data indicate that inhibition of Akt phosphorylation by some of the SH compounds is cell line specific, and that inhibition by SH5, 6, 13, 23-25 is not dependent on PTEN. FIG. 1E shows that SH5, 6, 23-25 inhibit Akt kinase activity, as well as Akt phosphorylation.

FIG. 1F shows results on some of the compounds. SH5, 6, 23, 24, and 25 completely inhibited Akt phosphorylation in all three cell lines and were chosen for further analysis.

Figure 2A:
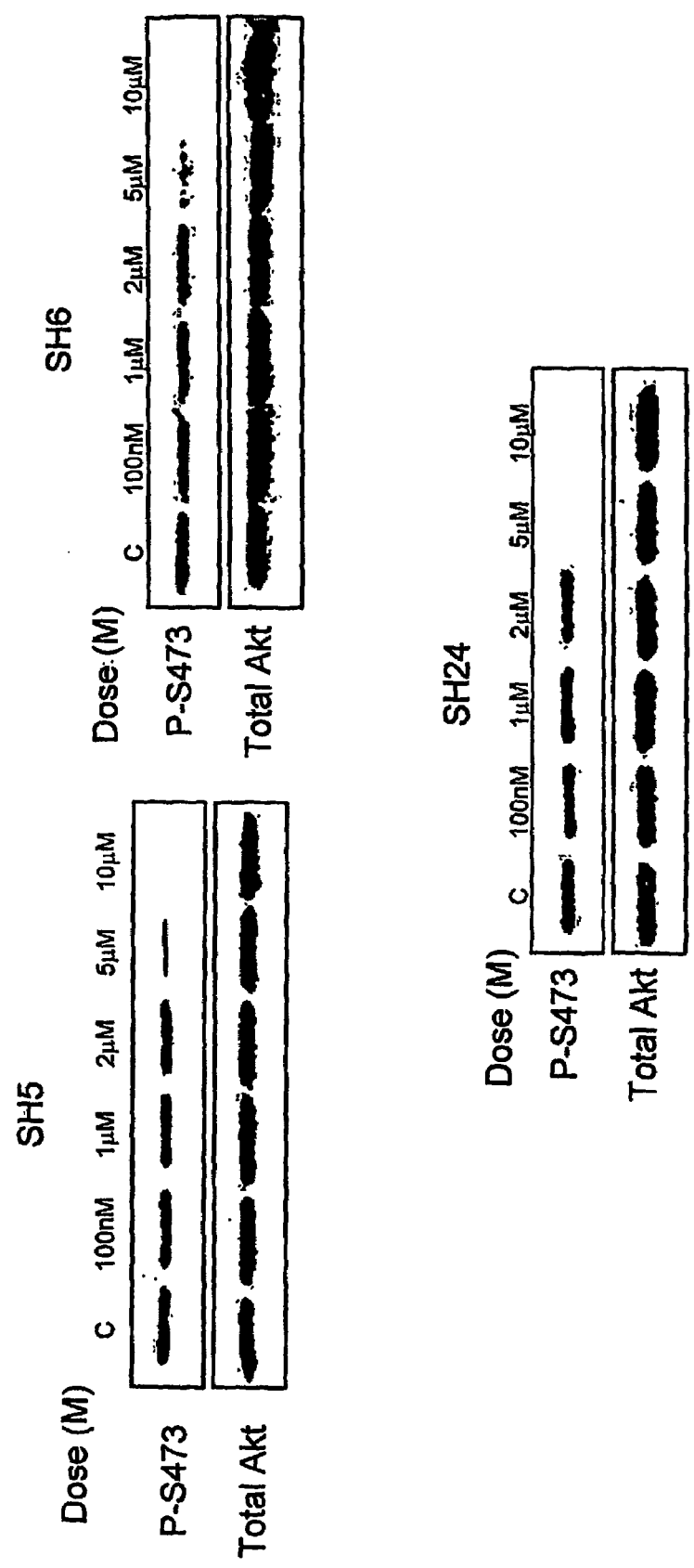
FIG. 2A depicts the dose response curve for some of the Akt inhibitors.
Figure 2B:
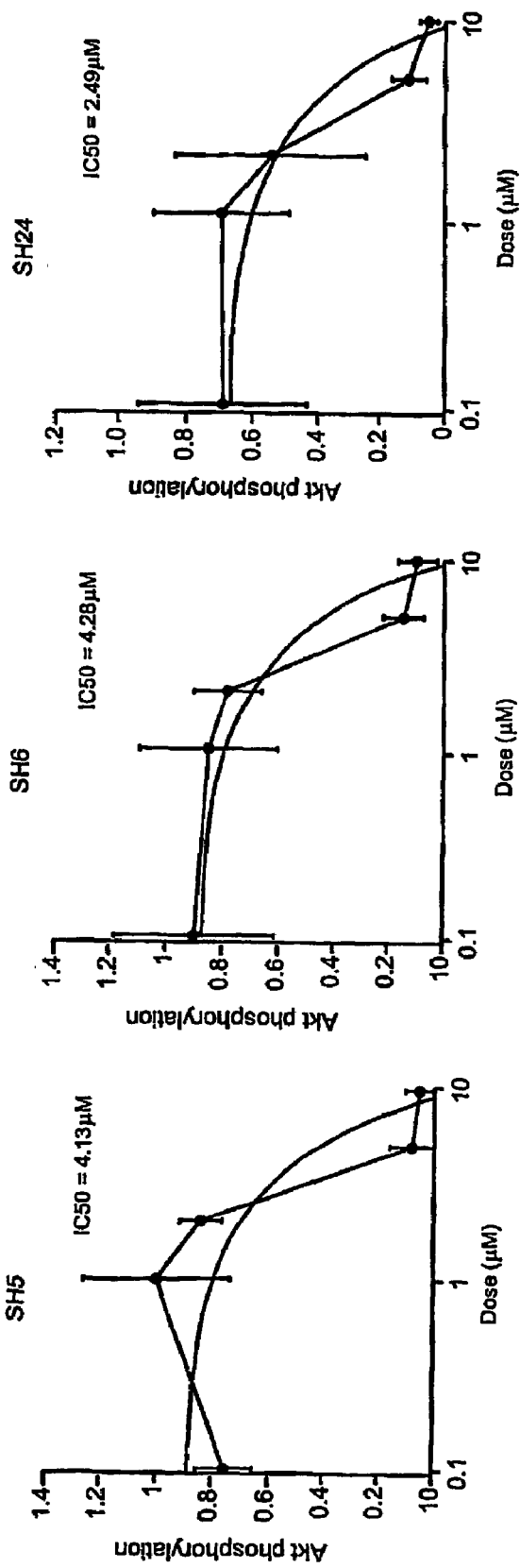
FIG. 2B depicts the dose response curves for some of the inhibitors on Akt phosphorylation.

FIG. 2A is a set of representative immunoblotting experiments with increasing doses of SH5, 6, and 24. For each set of immunoblotting experiments, densitometry was performed to quantify the decreased intensity of the bands observed with the S473 antibodies. Quantitative inhibition of S473 phosphorylation by different doses of these compounds is shown in FIG. 2B. The IC50 values for these compounds (including SH23 and 25 (data not shown)) were similar, between 2-4 µM.

Figure 3A:
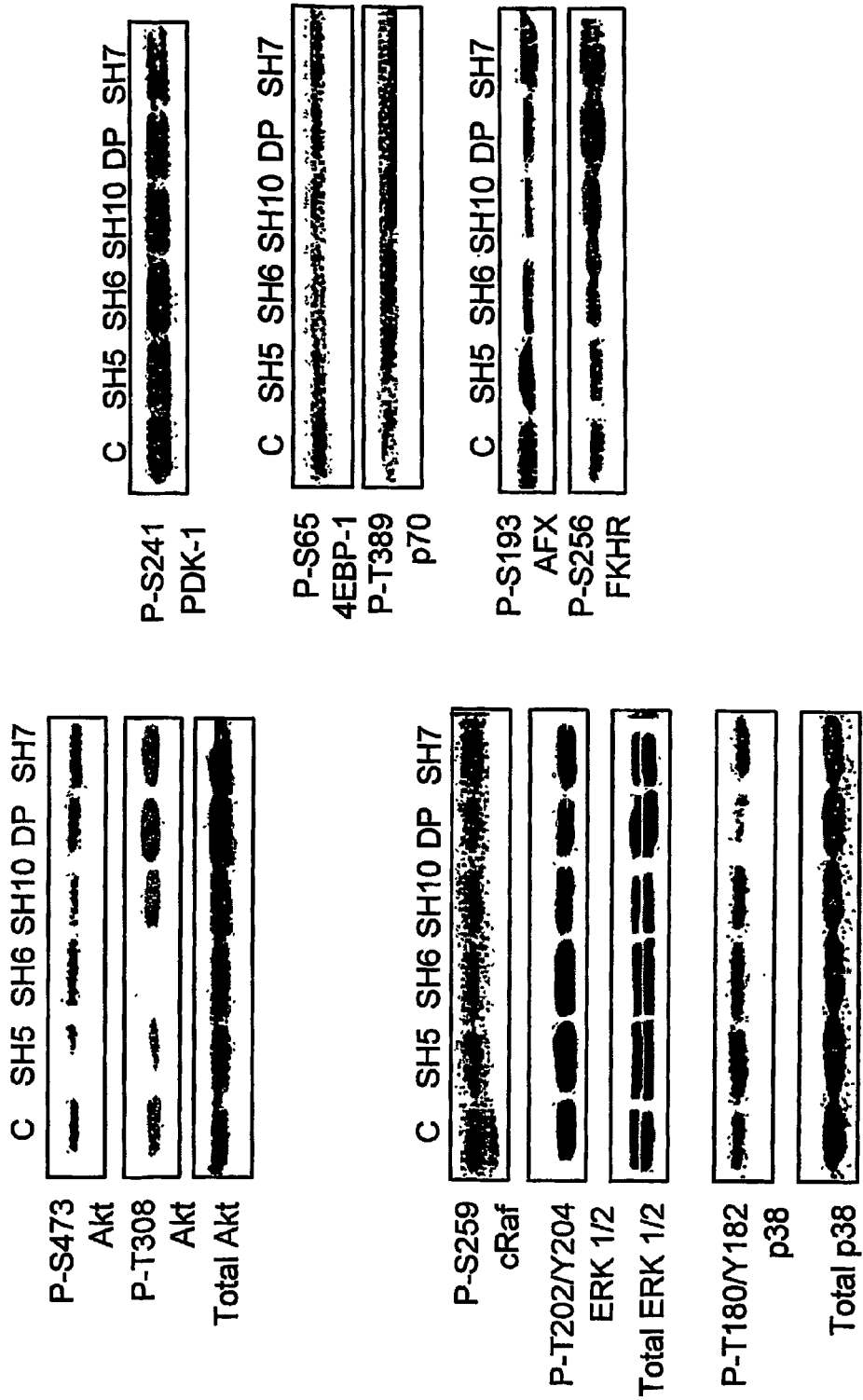
FIG. 3A depicts selectivity data for some of the Akt inhibitors on H1703 cells.
Figure 3B:
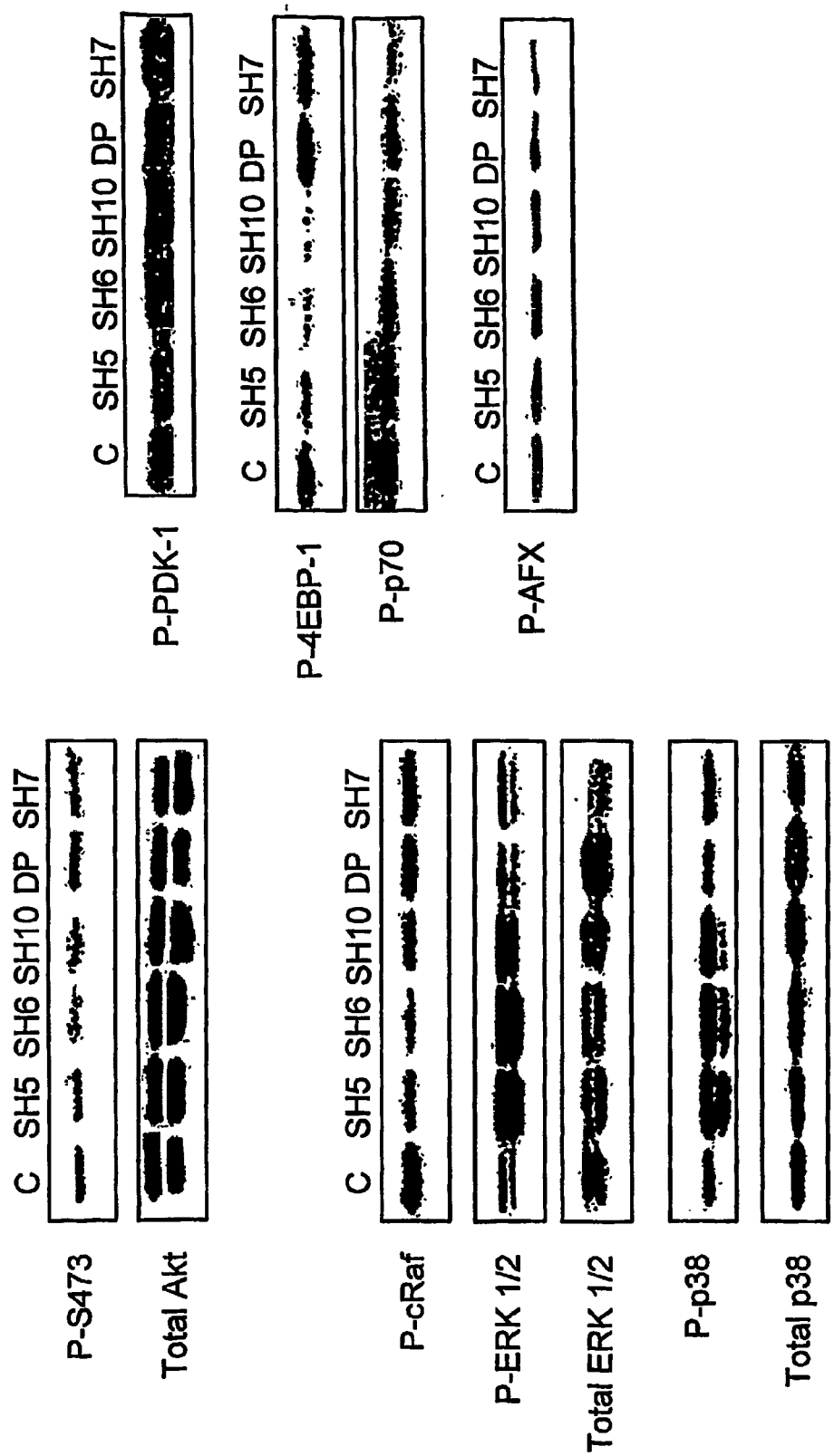
FIG. 3B depicts selectivity data for some of the Akt inhibitors on H157 cells.

The SH compounds were tested against Akt and other kinases that are either upstream of Akt (PDK-1), downstream of Akt (c-Raf, 4EBP-1, p70S6K, FKHR, GSK-3, and/or AFX), or downstream of Ras (ERK, p38). Immunoblotting was carried out with phospho-specific antibodies to assess activation state of the kinases, and with native antibodies to assess changes in protein levels. Similar results were obtained with the H1703 (FIG. 3A) or H157 cells (FIG. 3B). SH5, 6, and 10 inhibited Akt phosphorylation without affecting native Akt levels. DPIEL and SH7 did not decrease Akt phosphorylation. Upstream of Akt, phosphorylation of PDK-1 was not affected by any SH compound. Of the downstream substrates, c-Raf phosphorylation and 4EBP-1 phosphorylation were decreased most. Decreased c-Raf phosphorylation correlated with increased ERK and p38 phosphorylation, which is consistent with the inhibitory effect of S259 phosphorylation by Akt on c-Raf activity. Of note, p38 phosphorylation was only decreased by DPIEL, indicating that the DPIEL used in these experiments was not inert.

Figure 3C:
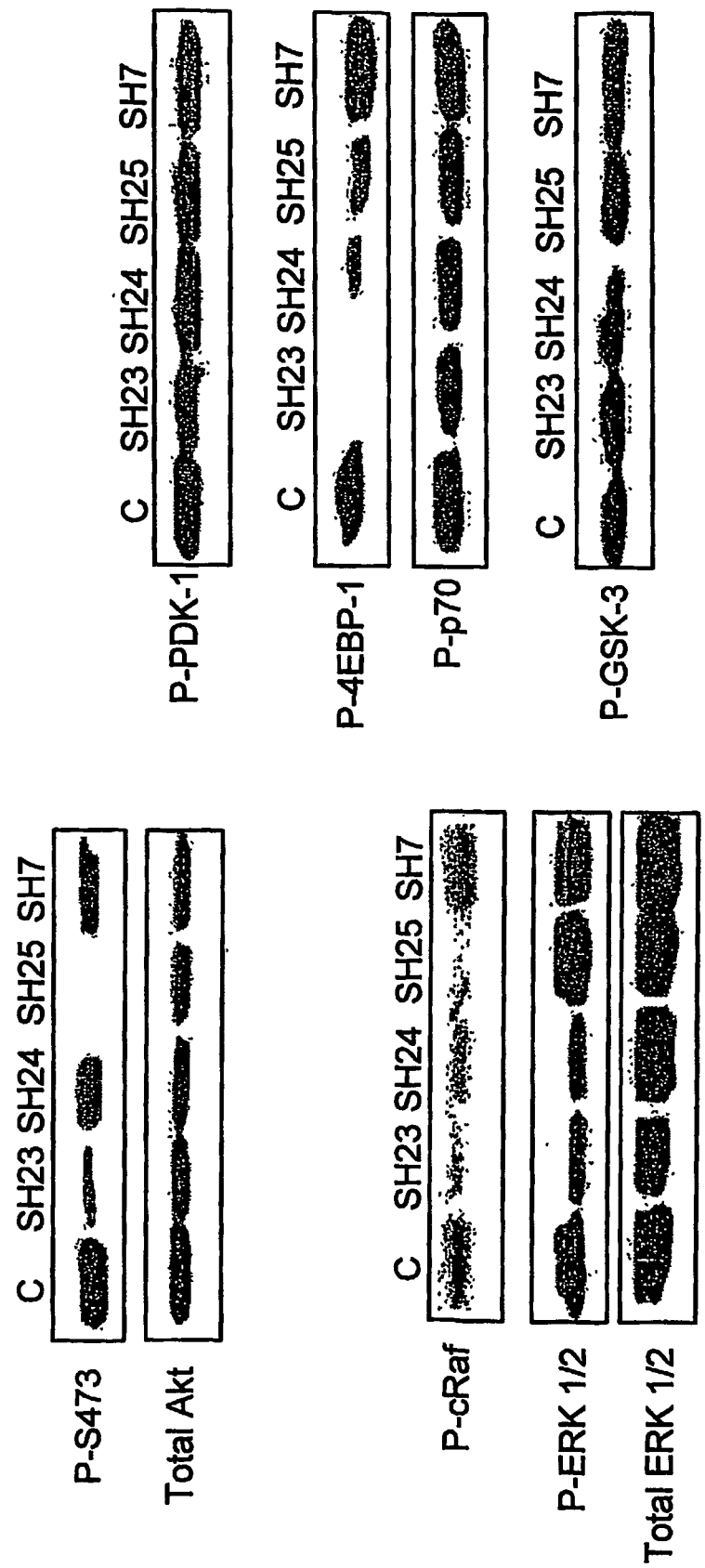
FIG. 3C depicts selectivity data for some of the Akt inhibitors (SH 23-25) on H1703 cells.
Figure 3D:
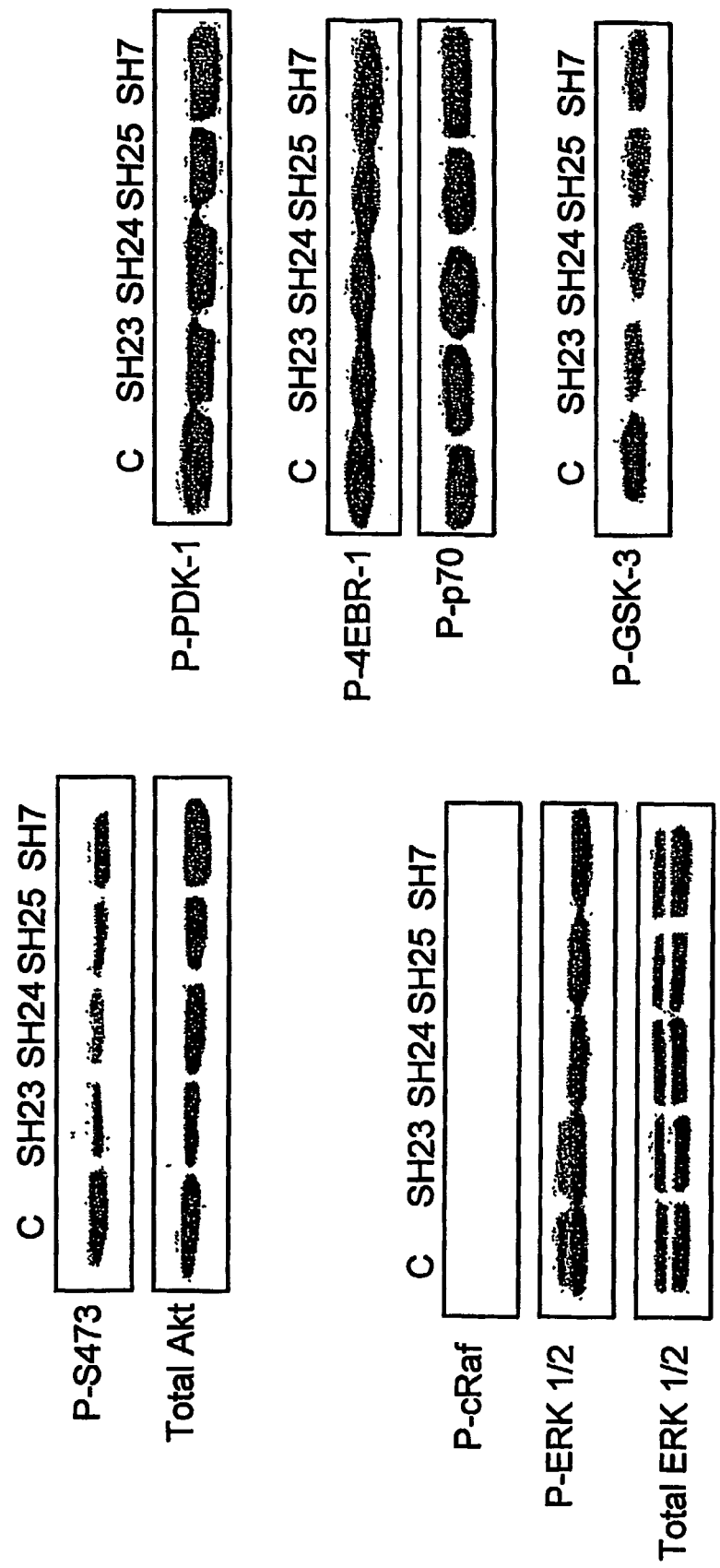
FIG. 3D depicts selectivity data for some of the Akt inhibitors on MB468 cells.

SH 23-25 had similar effects in both H1703 (FIG. 3C) and MB468 (FIG. 3D) cells (H157 data not shown). In H1703 cells, phosphorylation of Akt, c-Raf, and 4-EBP-1 was decreased by SH23-25, but PDK-1 phosphorylation was unaffected. MB468 cells decreased Akt phosphorylation with administration of SH23-25 without decreasing PDK-1 phosphorylation. Some effects of SH23-25 were unique to the MB468 cells. Because MB468 cells had little endogenous phosphorylated c-Raf, we could not evaluate inhibition of c-Raf. Phosphorylation of 4EBP-1 was not affected by SH23-25, but phosphorylation of GSK-3 was decreased.

Figure 4:
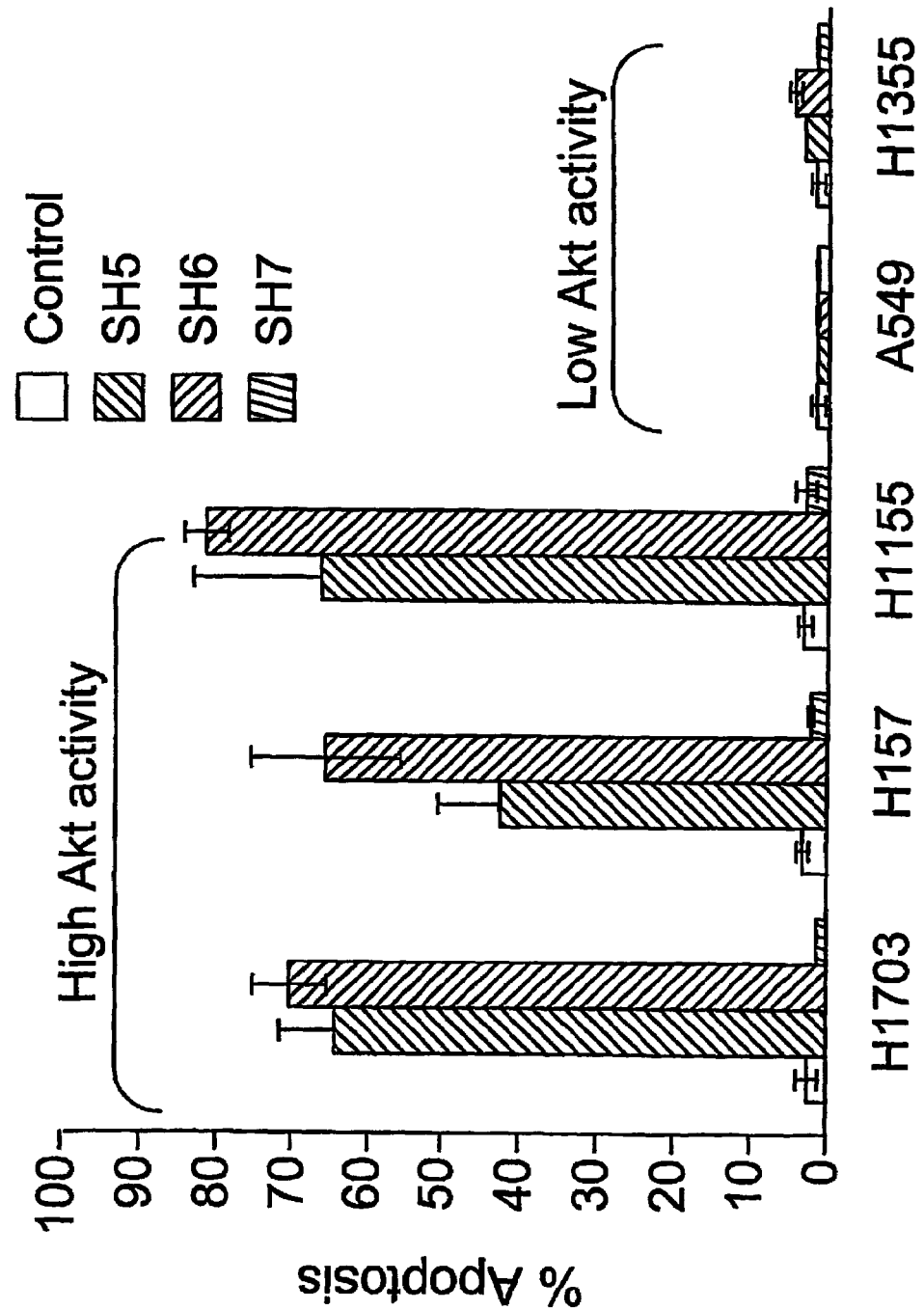
FIG. 4 depicts the increase of apoptosis by Akt inhibitors on cells with high levels of Akt activity.

Cell lines containing high or low endogenous levels of Akt activity were treated with SH compounds and the cell apoptosis was measured. As shown in FIG. 4, three cell lines with high levels of Akt activity, H1703, H157, and $H_{1155}$ cells, increased apoptosis by 10-20 fold with administration of SH5 or 6. Increased apoptosis was also observed with administration of SH5 or 6 in MB468 cells (data not shown). SH7 had no effect on apoptosis, similar to DPIEL (data not shown). In contrast to cells with high levels of Akt, cells with low endogenous Akt levels (H1355 and A549 cells) did not undergo apoptosis in response to SH5, 6, or 7.

SH5, 6, 23, 24, and 25 are very active in decreasing Akt phosphorylation in a panel of cancer cell lines. These compounds decrease Akt phosphorylation as well as Akt kinase activity, with IC50s in the low micromolar range. These compounds appear to be specific for Akt, as the phosphorylation of the upstream kinase, PDK-1, is unaffected by any of the SH compounds, as is phosphorylation of ERK and p38, which are downstream of Ras. Cell-line specific, selective inhibition of phosphorylation of substrates downstream of Akt, such as c-Raf, 4EBP-1, GSK-3, and/or FKHR/AFX was observed. These compounds selectively increased apoptosis in cancer cell lines that depend on Akt activity for survival. Phosphorylation of tuberin, 4EBP-1 and P70S6K (substrates that control protein translation) was inhibited by SH23, 24, and 25; and SH5-6 inhibited phosphorylation of tuberin and 4EBP-1. Phosphorylation of forkhead family members AFX and FKHR that control transcription was inhibited by SH23 or 25. Phosphorylation of GSK-3 and c-Raf was attenuated by SH23-25.

REFERENCES

1. Datta et al., M. E. Cellular survival: a play in three Akts. *Genes Dev.*, 13, 2905-2927 (1999).
2. Bellacosa et al., P. N. A retroviral oncogene, akt, encoding a serine-threonine kinase containing an SH2-like region. *Science*, 25, 274-277 (1991).
3. Coffer et al., Molecular cloning and characterisation of a novel putative protein-serine kinase related to the cAMP-dependent and protein kinase C families [published erratum appears in Eur J Biochem 1992 May 1; 205(3):1217]. *Eur J. Biochem.*, 201, 475-481 (1991).
4. Jones et al., Molecular cloning and identification of a serine/threonine protein kinase of the second-messenger subfamily. *Proc Natl Acad Sci USA*, 88, 4171-4175 (1991).
5. Balendran et al., PDK1 acquires PDK2 activity in the presence of a synthetic peptide derived from the carboxyl terminus of PRK2. *Curr Biol.*, 9, 393-404 (1999).
6. Delcommenne et al., Phosphoinositide-3-OH kinase-dependent regulation of glycogen synthase kinase 3 and protein kinase B/AKT by the integrin-linked kinase. *Proc Natl Acad Sci USA*, 95, 11211-11216 (1998).
7. Lynch et al., Integrin-linked kinase regulates phosphorylation of serine 473 of protein kinase B by an indirect mechanism. *Oncogene*, 18: 8024-8032 (1999).
8. Toker et al., Akt/protein kinase B is regulated by autophosphorylation at the hypothetical PDK-2 site. *J Biol. Chem.*, 275, 8271-8274 (2000).
9. Filippa et al., Mechanism of protein kinase B activation by cyclic AMP-dependent protein kinase. *Mol Cell Biol.*, 19, 4989-5000 (1999).
10. Yano et al., Calcium promotes cell survival through CaM-K kinase activation of the protein-kinase-B pathway. *Nature*, 396, 584-587 (1998).
11. Datta et al., Akt Phosphorylation of BAD Couples Survival Signals to the Cell-Intrinsic Death Machinery. *Cell*, 91, 231-241 (1997).
12. del Peso et al., Interleukin-3-induced phosphorylation of BAD through the protein kinase Akt. *Science*, 278, 687-689 (1997).
13. Cardone et al., Regulation of cell death protease caspase-9 by phosphorylation [see comments]. *Science*, 282, 1318-1321 (1998).
14. Kang et al., Akt protein kinase enhances human telomerase activity through phosphorylation of telomerase reverse transcriptase subunit. *J Biol. Chem.*, 274, 13085-13090 (1999).
15. Brunet et al., Akt promotes cell survival by phosphorylating and inhibiting a Forkhead transcription factor. *Cell*, 96, 857-868 (1999).
16. Kops et al., Direct control of the Forkhead transcription factor AFX by protein kinase B. *Nature*, 398, 630-634 (1999).
17. Ozes et al., NF-kappaB activation by tumour necrosis factor requires the Akt serine-threonine kinase [see comments]. *Nature*, 401, 82-85 (1999).
18. Romashkova et al., NF-kappaB is a target of AKT in anti-apoptotic PDGF signalling [see comments]. *Nature*, 401, 86-90 (1999).
19. Dudek et al., Regulation of Neuronal Survival by the Serine-Threonine Protein Kinase Akt. *Science*, 275, 661-665 (1997).
20. Kauffmann-Zeh et al., Suppresion of c-Myc-induced apoptosis by Ras signalling through PI(3)K and PKB. *Nature*, 385, 544-548 (1997).

21. Kennedy et al., Akt/Protein kinase B inhibits cell death by preventing the release of cytochrome c from mitochondria. *Mol Cell Biol.*, 19, 5800-5810 (1999).
22. Khwaja et al., Matrix adhesion and ras transformation both activate a phosphoinositide 3-OH kinase and protein kinase B/Akt cellular survival pathway. *The EMBO Journal*, 16, 2783-2793 (1997).
23. Kulik et al., Antiapoptotic Signalling by the Insulin-Like Growth Factor I Receptor, Phosphatidylinositol 3-Kinase, and Akt. *Molecular and Cellular Biology*, 17, 1595-1606 (1997).
24. Chen et al., Suppression of transforming growth factor-beta-induced apoptosis through a phosphatidylinositol 3-kinase/Akt-dependent pathway. *Oncogene*, 17, 1959-1968 (1998).
25. Crowder et al., Phosphatidylinositol 3-kinase and Akt protein kinase are necessary and sufficient for the survival of nerve growth factor-dependent sympathetic neurons. *J Neurosci*, 18, 2933-2943 (1998).
26. Eves et al., N. Akt, a target of phosphatidylinositol 3-kinase, inhibits apoptosis in a differentiating neuronal cell line. *Mol Cell Biol.*, 18, 2143-2152 (1998).
27. Blair et al., Akt-dependent potentiation of L channels by insulin-like growth factor-1 is required for neuronal survival. *J Neurosci*, 19, 1940-1951 (1999).
28. Gerber et al., Vascular endothelial growth factor regulates endothelial cell survival through the phosphatidylinositol 3'-kinase/Akt signal transduction pathway. Requirement for Flk-1/KDR activation. *J Biol. Chem.*, 273, 30336-30343 (1998).
29. Hausler et al., Protection of CD95-mediated apoptosis by activation of phosphatidylinositide 3-kinase and protein kinase B. *Eur J Immunol*, 28, 57-69 (1998).
30. Kulik et al. Akt-dependent and -independent survival signaling pathways utilized by insulin-like growth factor I. *Mol Cell Biol.*, 18, 6711-6718 (1998).
31. Robn et al., The opposing roles of the Akt and c-Myc signalling pathways in survival from CD95-mediated apoptosis. *Oncogene*, 17, 2811-2818 (1998).
32. Chalecka-Franaszek et al., Lithium activates the serine/threonine kinase Akt-1 and suppresses glutamate-induced inhibition of Akt-1 activity in neurons. *Proc Natl Acad Sci U S A*, 96, 8745-8750 (1999).
33. Rust et al., The bile acid taurochenodeoxycholate activates a phosphatidylinositol 3-kinase-dependent survival signaling cascade [In Process Citation]. *J Biol. Chem.*, 275, 20210-20216 (2000).
34. Testa., AKT plays a central role in tumorigenesis. *Proc Natl Acad Sci USA*, 98, 10983-10985 (2001).
35. Brognard et al., Akt/protein kinase b is constitutively active in non-small cell lung cancer cells and promotes cellular survival and resistance to chemotherapy and radiation. *Cancer Res.*, 61, 3986-3997 (2001).
36. Clark et al., Constitutive and inducible Akt activity promotes resistance to chemotherapy, trastuzumab, and tamoxifen in breast cancer cells. *Molec Canc Ther.*, 1, 707-717 (2002).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:
1. A compound of the formula I:

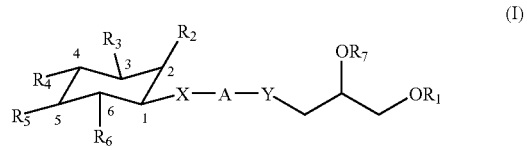

or a pharmaceutically acceptable salt thereof
wherein X and Y are independently selected from the group consisting of O, $CF_2$, $CH_2$, and CHF;
wherein A is P(O)OH;
$R_2$ is selected from the group consisting of H, OH, $C_1$-$C_{25}$ alkyloxy, $C_6$-$C_{10}$ aryloxy, $C_3$-$C_8$ cycloalkyloxy, $C_3$-$C_8$ cycloalkyl $C_1C_6$ alkoxy, $C_2$-$C_{22}$ alkenyloxy, $C_3C_8$ cycloalkenyloxy, $C_7$-$C_{32}$ aralkyloxy, $C_7C_{32}$ alkylaryloxy, $C_9$-$C_{32}$ aralkenyloxy, and $C_9$-$C_{32}$ alkenylaryloxy;
$R_3$-$R_6$ are independently selected from the group consisting of H and OH; and
$R_1$ and $R_7$ are independently selected from the group consisting of $C_1C_{25}$ alkyl, $C_6$-$C_{10}$ aryl, $C_3$-$C_8$ cycloalkyl, $C_2$-$C_{22}$ alkenyl, $C_3$-$C_8$ cycloalkenyl, $C_7$-$C_{32}$ aralkyl, $C_7$-$C_{32}$ alkylaryl, $C_9$-$C_{32}$ aralkenyl, and $C_9$-$C_{32}$ alkenylaryl;
with the provisos that (i) when X is O, Y is O or $CH_2$, and $R_3$ is H, at least one of $R_2$ and $R_4$-$R_6$ is not OH; (ii) all of $R_2$-$R_6$ are not simultaneously H; (iii) $R_5$ and $R_4$ are not simultaneously H; (iv) $R_2$, $R_3$, $R_5$, and $R_6$ are not simultaneously OH or H and (v) when X and Y are O, $R_1$ is $C_{18}H_{37}$, and only one of $R_2$ and $R_6$ is $OCH_3$, then $R_3$ and $R_5$ are not simultaneously OH.

2. The compound of claim 1, which has the formula Ia:

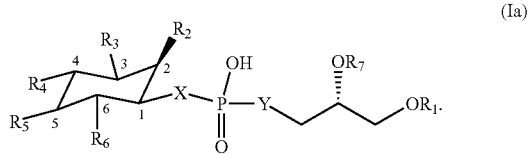

or a pharmaceutically acceptable salt thereof.

3. The compound of claim 1, which has the formula Ib:

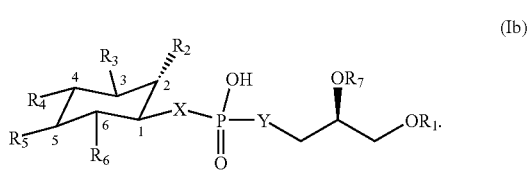

or a pharmaceutically acceptable salt thereof.

4. The compound or a pharmaceutically acceptable salt of claim 1, wherein X and Y are O.

5. The compound or a pharmaceutically acceptable salt of claim 1, wherein $R_1$ is a $C_1$-$C_{25}$ alkyl.

6. The compound or a pharmaceutically acceptable salt of claim 1, wherein $R_1$ is a $C_{10}$-$C_{25}$ alkyl.

7. The compound or a pharmaceutically acceptable salt of claim 1, wherein $R_1$ is a $C_{15}$-$C_{20}$ alkyl.

8. The compound or a pharmaceutically acceptable salt of claim 1, wherein $R_1$ is a $C_{18}$ alkyl.

9. The compound or a pharmaceutically acceptable salt of claim 1, wherein $R_7$ is a $C_1$-$C_{25}$ alkyl.

10. The compound or a pharmaceutically acceptable salt of claim 1, wherein $R_7$ is a $C_1$-$C_{15}$ alkyl.

11. The compound or a pharmaceutically acceptable salt of claim 1, wherein $R_7$ is a $C_1$-$C_5$ alkyl.

12. The compound or a pharmaceutically acceptable salt of claim 1, wherein $R_7$ is methyl.

13. The compound or a pharmaceutically acceptable salt of claim 1, wherein $R_2$ is $C_1$-$C_{25}$ alkyloxy.

14. The compound or a pharmaceutically acceptable salt of claim 1, wherein $R_2$ is $C_1$-$C_{15}$ alkyloxy.

15. The compound or a pharmaceutically acceptable salt of claim 1, wherein $R_2$ is $C_1$-$C_5$ alkyloxy.

16. The compound or a pharmaceutically acceptable salt of claim 1, wherein $R_2$ is methoxy.

17. The compound or a pharmaceutically acceptable salt of claim 1, wherein $R_2$ is $C_7$-$C_{32}$ aralkyloxy.

18. The compound or a pharmaceutically acceptable salt of claim 1, wherein $R_2$ is cyclohexylmethoxy.

19. The compound or a pharmaceutically acceptable salt of claim 1, wherein $R_2$ is H.

20. The compound or a pharmaceutically acceptable salt of claim 1, wherein $R_3$ is H.

21. The compound or a pharmaceutically acceptable salt of claim 1, wherein $R_4$ is H.

22. The compound or a pharmaceutically acceptable salt of claim 1, wherein $R_5$ is H.

23. The compound or a pharmaceutically acceptable salt of claim 1, wherein $R_6$ is H.

24. The compound or a pharmaceutically acceptable salt of claim 1, wherein $R_2$ and $R_3$ are H.

25. The compound or a pharmaceutically acceptable salt of claim 1, wherein $R_3$ and $R_4$ are H.

26. The compound or a pharmaceutically acceptable salt of claim 1, wherein $R_5$ and $R_6$ are H.

27. The compound or a pharmaceutically acceptable salt of claim 2, wherein X and Y are O, $R_1$ is $C_{18}H_{37}$, and $R_7$ methyl.

28. The compound or a pharmaceutically acceptable salt of claim 27, wherein $R_2$ is methoxy, $R_3$ is H, and $R_4$-$R_6$ are OH.

29. The compound or a pharmaceutically acceptable salt of claim 27, wherein $R_2$-$R_3$ are H and $R_4$-$R_6$ are OH.

30. A compound of the formula:

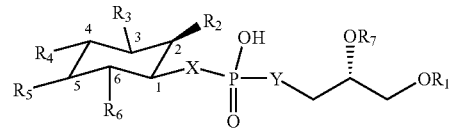

wherein X and Y are O, $R_1$ is $C_{18}H_{37}$, and $R_7$ is methyl; and $R_2$-$R_3$ and $R_5$-$R_6$ are OH and $R_4$ is H or a pharmaceutically acceptable salt thereof.

31. The compound or a pharmaceutically acceptable salt of claim 28, wherein $R_2$ is i-butyloxy, $R_3$ is H, and $R_4$-$R_6$ are OH.

32. The compound of claim 28, wherein $R_2$ is cyclohexylmethoxy, $R_3$ is H, and $R_4$-$R_6$ are OH.

33. A compound of the formula:

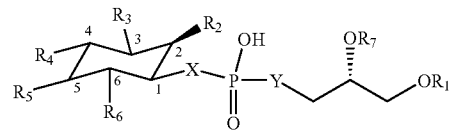

wherein X and Y are O, $R_1$ is $C_{18}H_{37}$ $R_7$, is methyl, $R_2$-$R_3$ and $R_6$ are OH, and $R_4$-$R_5$ are H or a pharmaceutically acceptable salt.

34. The compound or a pharmaceutically acceptable salt of claim 27, wherein $R_2$-$R_4$ and $R_6$ are OH and $R_5$ is H.

35. The compound or a pharmaceutically acceptable salt of claim 27, wherein $R_2$, $R_4$, and $R_6$ are OH and $R_3$ and $R_5$ are H.

36. A pharmaceutical composition comprising a compound or a pharmaceutically acceptable salt of claim 1 and a pharmaceutically acceptable carrier.

37. A method of inhibiting activation of the serine/threonine kinase Akt or decreasing phosphorylation in a tumor cell of an animal comprising administering to the animal an effective amount of a compound or a pharmaceutically acceptable salt of claim 1.

38. A method of increasing apoptosis of a cell comprising contacting the cell with a compound or a pharmaceutically acceptable salt of claim 1.

39. A method for inhibiting PH domain binding comprising exposing a material containing an PH domain to a compound or a pharmaceutically acceptable salt of claim 1.

40. A method for determining the presence of a PH domain in a material comprising:
   (a) exposing a sample of said material to a PH domain binding compound and obtaining a first binding result;
   (b) exposing another sample of said material to a compound or a pharmaceutically acceptable salt of claim 1 and obtaining a second binding result; and (c) comparing the first and second binding results to determine whether a PH domain is present in the material.

41. A method of treating cancer in a mammal comprising administering to the mammal an effective amount of a compound or a pharmaceutically acceptable salt of claim 1, wherein the cancer is selected from the group consisting of lung cancer, breast cancer, ovarian cancer, colorectal cancer, and brain cancer.

42. A compound of the formula I:

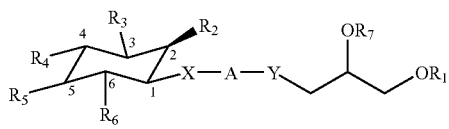

or a pharmaceutically acceptable salt thereof
wherein X and Y are independently selected from the group consisting of O, $CF_2$, $CH_2$, and CHF;
wherein A is P(O)OH;
$R_2$ is selected from the group consisting of $C_1$-$C_{25}$ alkyloxy, cyclohexylmethoxy, and $C_7$-$C_{32}$ aralkyloxy;
$R_3$-$R_6$ are independently selected from the group consisting of H, $R_1$ and $R_7$ are independently selected from the group consisting of $C_1$-$C_{25}$ alkyl, $C_6$-$C_{10}$ aryl, $C_3$-$C_8$ cycloalkyl, $C_2$-$C_{22}$ alkenyl, $C_3$-$C_8$ cycloalkenyl, $C_7$-$C_{32}$ aralkyl, $C_7$-$C_{32}$ alkylaryl, $C_9$-$C_{32}$ aralkenyl, and $C_9$-$C_{32}$ alkenylaryl;
with the provisos that (i) when X is O, Y is O or $CH_2$, and $R_3$ is H, at least one of $R_2$ and $R_4$-$R_6$ is not OH; (ii) all of $R_2$-$R_6$ are not simultaneously H; and when X and Y are O, $R_1$ is $C_{18}H_{37}$, and only one of $R_2$ and $R_6$ is $OCH_3$, then $R_3$ and $R_5$ are not simultaneously OH.

43. The compound or a pharmaceutically acceptable salt of claim 42, wherein $R_2$ is $C_1$-$C_{25}$ alkyloxy.

44. The compound or a pharmaceutically acceptable salt of claim 42, wherein $R_2$, is $C_7$-$C_{32}$ aralkyloxy.

45. The compound or a pharmaceutically acceptable salt of claim 42, wherein $R_2$ is cyclohexylmethoxy.

46. The compound or a pharmaceutically acceptable salt of claim 42, wherein $R_3$ and $R_4$ are H.

47. The compound of claim 42, which has the formula Ia:

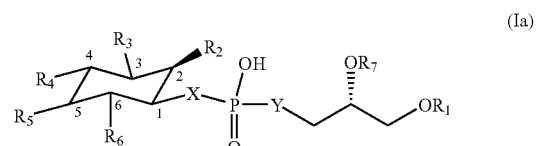

wherein X and Y are O, $R_1$ is $C_{18}H_{37}$, $R_7$ is methyl, $R_2$ is methoxy, $R_3$ is H, and $R_4$-$R_6$ are OH or a pharmaceutically acceptable salt thereof.

48. A method of increasing apoptosis of a cell comprising contacting the cell with a compound or a pharmaceutically acceptable salt of claim 42.

49. A method for inhibiting PH domain binding comprising exposing a material containing an PH domain to a compound or a pharmaceutically acceptable salt of claim 42.

50. A pharmaceutical composition comprising a compound or a pharmaceutically acceptable salt of claim 42 and a pharmaceutically acceptable carrier.

51. A method of treating cancer in a mammal comprising administering to the mammal an effective amount of a compound or a pharmaceutically acceptable salt of claim 42, wherein the cancer is selected from the group consisting of lung cancer, breast cancer, ovarian cancer, colorectal cancer, and brain cancer.

52. A method of inhibiting activation of the serine/threonine kinase Akt or decreasing phosphorylation in a tumor cell of an animal comprising administering to the animal an effective amount of a compound or a pharmaceutically acceptable salt of claim 42.

53. A pharmaceutical composition comprising a compound or a pharmaceutically acceptable salt of claim 30 and a pharmaceutically acceptable carrier.

54. A pharmaceutical composition comprising a compound or a pharmaceutically acceptable salt of claim 33 and a pharmaceutically acceptable carrier.

* * * * *